US011253473B2

(12) United States Patent
Bruun et al.

(10) Patent No.: US 11,253,473 B2
(45) Date of Patent: Feb. 22, 2022

(54) METHOD OF PRODUCING TABLETED CANNABINOID CHEWING GUM

(71) Applicant: NordicCan A/S, Vejle (DK)

(72) Inventors: Heidi Ziegler Bruun, Vejle O (DK); Dorthe Schackinger Boesen, Vejle (DK); Ane Eriksen, Vejle (DK)

(73) Assignee: NORDICCAN A/S, Vejle (DK)

(*) Notice: Subject to any disclaimer, the term of this patent is extended or adjusted under 35 U.S.C. 154(b) by 0 days.

(21) Appl. No.: 16/289,810

(22) Filed: Mar. 1, 2019

(65) Prior Publication Data

US 2020/0276117 A1    Sep. 3, 2020

(51) Int. Cl.
| | | |
|---|---|---|
| *A61K 9/68* | (2006.01) | |
| *A61K 31/352* | (2006.01) | |
| *A61K 9/00* | (2006.01) | |
| A61K 31/485 | (2006.01) | |
| A61K 47/44 | (2017.01) | |
| A61K 47/12 | (2006.01) | |
| A61K 47/26 | (2006.01) | |
| A61K 47/38 | (2006.01) | |
| A61K 47/10 | (2017.01) | |
| A61K 9/107 | (2006.01) | |

(52) U.S. Cl.
CPC ............ *A61K 9/0058* (2013.01); *A61K 9/006* (2013.01); *A61K 31/352* (2013.01); *A61K 9/107* (2013.01); *A61K 31/485* (2013.01); *A61K 47/10* (2013.01); *A61K 47/12* (2013.01); *A61K 47/26* (2013.01); *A61K 47/38* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 6,017,566 A | 1/2000 | Bunczek et al. | |
| 8,137,716 B2 | 3/2012 | Mikkelsen et al. | |
| 9,023,322 B2 | 5/2015 | Van Damme et al. | |
| 9,433,601 B2 | 9/2016 | Van Damme et al. | |
| 9,744,128 B2 | 8/2017 | Bachmann et al. | |
| 9,833,408 B1 * | 12/2017 | Greenspoon | A61K 9/0058 |
| 2004/0028772 A1 | 2/2004 | Andersen | |
| 2009/0298929 A1 | 12/2009 | Jarho et al. | |
| 2015/0209322 A1 | 7/2015 | Van Damme et al. | |
| 2016/0220593 A1 | 8/2016 | Anastassov et al. | |
| 2016/0354310 A1 * | 12/2016 | Bachmann | A23G 4/12 |
| 2017/0265494 A1 | 9/2017 | Uccello, III | |
| 2017/0273902 A1 | 9/2017 | Bachmann et al. | |
| 2017/0273903 A1 | 9/2017 | Bachmann et al. | |
| 2017/0281539 A1 | 10/2017 | Bachmann et al. | |
| 2017/0312261 A1 | 11/2017 | Changoer et al. | |
| 2017/0326126 A1 * | 11/2017 | Williams | A61K 9/7038 |
| 2017/0368020 A1 | 12/2017 | Estey et al. | |
| 2018/0064645 A1 | 3/2018 | Greenspoon | |
| 2018/0110730 A1 | 4/2018 | Changoer et al. | |
| 2018/0147141 A1 | 5/2018 | Changoer et al. | |
| 2018/0206518 A1 | 7/2018 | Silver | |
| 2019/0060229 A1 | 2/2019 | Neergaard et al. | |

FOREIGN PATENT DOCUMENTS

| | | | |
|---|---|---|---|
| CA | 2719830 C | 10/2009 | |
| CA | 2937471 A1 | 9/2016 | |
| CA | 2999032 A1 | 3/2017 | |
| CA | 3025559 A1 | 11/2017 | |
| CA | 3031530 A1 | 12/2019 | |
| EP | 1474993 A1 | 11/2004 | |
| EP | 1474995 A1 * | 11/2004 | ............ A23G 3/004 |
| EP | 1474995 A1 | 11/2004 | |
| EP | 1554935 A1 | 7/2005 | |
| WO | 2004004479 A1 | 1/2004 | |

(Continued)

OTHER PUBLICATIONS

S. O. Vargas Nunes, et al. The shared role of oxidative stress and inflammation in major depressive disorder and nicotine dependence, Neuroscience & Biobehavioral Reviews, vol. 37, Issue 8, 2013, pp. 1336-1345, (Year: 2013).*

Cornell University Law School, citing 10 U.S. Code § 1074g(i)(2), defines the term "pharmaceutical agent", https://www.law.cornell.edu/uscode/ text/10/1074g#i_2; downloaded Jun. 4, 2021. (Year: 2016).*

T. Strause ("Full Spectrum Hemp Oil vs CBD Isolate," downloaded Jul. 29, 2020 from https://medium.com/randy-s-club/how-hemp-oil-heals-cd0e0154bd51; available on the internet Sep. 21, 2017), (Year: 2017).*

(Continued)

*Primary Examiner* — Michael P Cohen

(74) *Attorney, Agent, or Firm* — Gregory M. Howison

(57) ABSTRACT

The present invention relates to a method of producing a tableted chewing gum composition for oral administration of cannabinoids, the method comprises the steps of: i) feeding a gum composition comprising water-insoluble gum base into an extruder from one or more feeding inlets, optionally including additional ingredients, ii) pressurizing the gum composition in the extruder while controlling temperature and pressure of the gum composition, optionally including further ingredients from one or more feeding inlets, iii) extruding the gum composition through a die means, iv) cutting the extruded gum composition in a liquid filled chamber, thereby obtaining a first population of particles comprising water-insoluble gum base, v) including the first population of particles with a second population of particles comprising water-soluble chewing gum ingredients and one or more cannabinoids, the second population of particles being free of water-insoluble gum base, thereby obtaining a chewing gum composition and vi) tableting the chewing gum composition in a tablet pressing apparatus, thereby obtaining a tableted chewing gum composition.

31 Claims, 2 Drawing Sheets

(56) References Cited

FOREIGN PATENT DOCUMENTS

| WO | 2006063189 A2 | 6/2006 | | |
|---|---|---|---|---|
| WO | 2009006899 A1 | 1/2009 | | |
| WO | 2009007769 A1 | 1/2009 | | |
| WO | 2009080020 A1 | 7/2009 | | |
| WO | 2009080021 A1 | 7/2009 | | |
| WO | 2009120080 A1 | 10/2009 | | |
| WO | WO2009120080 A1 | 10/2009 | | |
| WO | 2015154780 A1 | 10/2015 | | |
| WO | WO2016126592 A1 | 8/2016 | | |
| WO | WO2017053731 A1 | 3/2017 | | |
| WO | WO2017059859 A1 | 4/2017 | | |
| WO | 2017189375 A1 | 11/2017 | | |
| WO | 2017202424 A1 | 11/2017 | | |
| WO | WO2017189375 A1 | 11/2017 | | |
| WO | WO-2017202424 A1 * | 11/2017 | ........... | A61K 9/2013 |
| WO | WO2017223309 A1 | 12/2017 | | |
| WO | WO2018006165 A1 | 1/2018 | | |
| WO | 2018018152 A1 | 2/2018 | | |
| WO | WO2018018152 A1 | 2/2018 | | |
| WO | 2018075665 A1 | 4/2018 | | |
| WO | WO2018075665 A1 | 4/2018 | | |
| WO | 2018091048 A1 | 5/2018 | | |
| WO | 2019219147 A1 | 11/2019 | | |

OTHER PUBLICATIONS

American Dental, "Chewing Gum". Sep. 2016. Downloaded Sep. 23, 2019 from https://web.archive.org/web/20160915140233/https//www.ada.org/en/member-center/oral-health-topics/chewing-gum, 3 pages.

Elsohly et al., "Phytochemistry of *Cannabis sativa* L.," 2017. Kinghorn et al. (Eds ), Phytocannabinnoids Progress in the Chemistry of Organic Natural Products 103. 34 pages.

Leizer et al.,"The Composition of Hemp Seed Oil and Its Potential as an Important Source of Nutrition," 2000. Journal of Nutraceuticals, functional & medical foods. 2(4): 35-53.

Patent Cooperation Treaty: International Search Report and Written Opinion of PCT/DK2019/050302; Bondar, Daniela; Feb. 3, 2020; 12 pages.

Patent Cooperation Treaty: International Search Report and Written Opinion of PCT/DK2019/050303; Bondar, Daniela; Feb. 3, 2020; 12 pages.

Patent Cooperation Treaty: International Search Report and Written Opinion of PCT/DK2019/050304; Bondar, Daniela; Feb. 3, 2020; 11 pages.

Patent Cooperation Treaty: International Search Report and Written Opinion of PCT/DK2019/050305; Couckuyt, Philippe; Jan. 31, 2020; 13 pages.

Patent Cooperation Treaty: International Search Report and Written Opinion of PCT/DK2019/050306; Couckuyt, Philippe; Jan. 31, 2020 ; 12 pages.

Patent Cooperation Treaty: International Search Report and Written Opinion of PCT/DK2019/050307; Couckuyt, Philippe; Feb. 12, 2020; 13 pages.

Patent Cooperation Treaty: International Search Report and Written Opinion of PCT/DK2019/050308; Bondar, Daniela; Feb. 3, 2020; 11 pages.

Patent Cooperation Treaty: International Search Report and Written Opinion of PCT/DK2019/050309; Bondar, Daniela; Feb. 3, 2020; 11 pages.

Patent Cooperation Treaty: International Search Report and Written Opinion of PCT/DK2019/050310; Couckuyt, Philippe; Feb. 12, 2020; 13 pages.

Patent Cooperation Treaty: International Search Report and Written Opinion of PCT/DK2019/050311; Couckuyt, Philippe; Feb. 12, 2020; 13 pages.

* cited by examiner

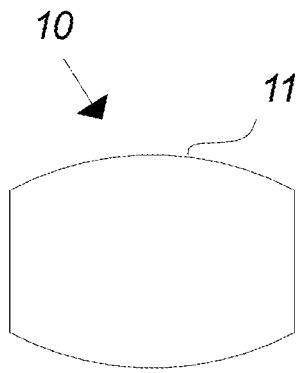
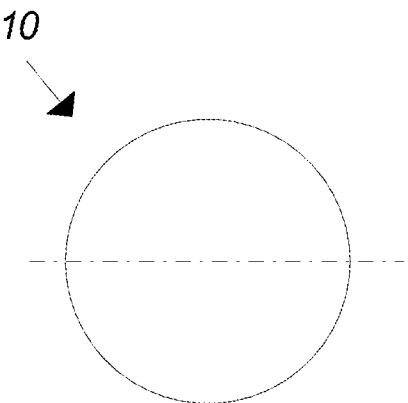
*Fig.1a*  *Fig.1b*
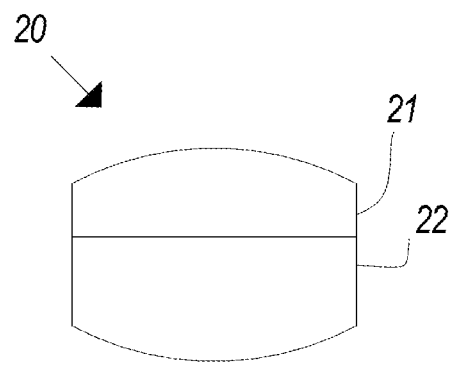
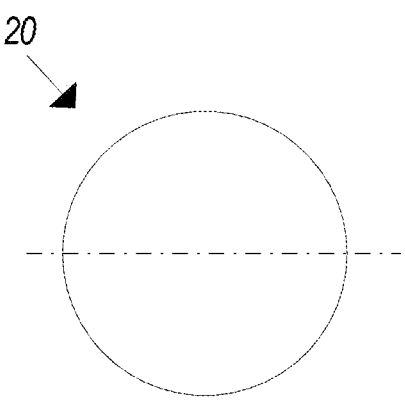
*Fig.2a*  *Fig.2b*
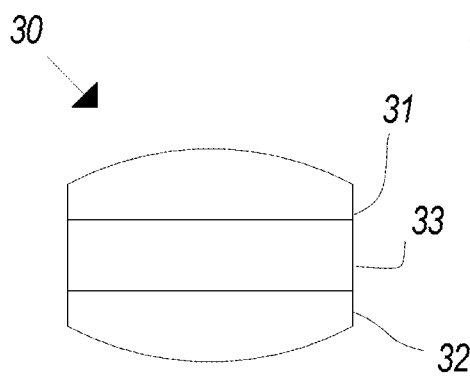
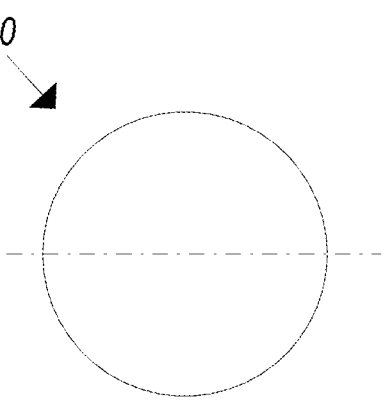
*Fig.3a*  *Fig.3b*

METHOD OF PRODUCING TABLETED CANNABINOID CHEWING GUM

FIELD OF THE INVENTION

The invention relates to the field of cannabinoids and alleviation or treatment of a condition with one or more cannabinoids. In particular, the invention relates to a method of producing a tableted chewing gum as a vehicle for oral administration of one or more cannabinoids.

BACKGROUND OF THE INVENTION

Cannabinoids are known for their health improving properties and have been used with respect to various medical purposes in the past. Among these medical purposes, cannabinoids have in particular been used for alleviating or treating different kinds of pain and counteracting side effects in relation to cancer treatment, such as nausea.

One way of administering cannabinoids is by inhalation or smoking. A problem related to such administration is that rapid blood absorption via the lungs may be undesirable. Smoking may not only have certain side effects, but the administration of cannabinoids may also be difficult to manage with respect to safety.

US 2016/0354310 discloses a method of producing cannabinoid chewing gum as a medical carrier of cannabinoids. The method disclosed herein involve heating of gum base in a container together with a sugar alcohol and discharging the melted gum base mixture into a separate container where another sugar alcohol mixture is present. After the mixture has been mixed for a period, the mixture is subsequently milled into a desired particle range and tableted in a tableting apparatus. However, various problems and challenges are associated with the chewing gum disclosed. While the procedure may require extensive manual labor work, the process may also involve problems with the sticking nature of gum base during the process of mixing, milling and tableting.

In general, less attention is addressed in the prior art of cannabinoids to methods of producing tableted cannabinoid chewing gum compositions that involve a smooth, economically beneficial and automated procedure. Also, less attention is given on the impact of the chewing gum platform and the choice of gum bases used in the production process for the sensorics properties of chewing gum with cannabinoids as well as release improving properties. Here, important sensorics properties include initial chew, texture, flavor perception, sweetness perception and off-notes associated with cannabinoids. These properties are both relevant from a convenience perspective in chewing gum, but certainly also in order to support an appropriate delivery of cannabinoids from chewing gum and avoid adverse side effects of cannabinoids.

Hence, there is a need in the prior art for improved methods of producing tableted cannabinoid chewing gum formulations that solve the above-referenced challenges and problems of the prior art. In particular, there is a need in the prior art for new chewing gum platforms and gum base formulations for use in chewing gum that support appropriate delivery of cannabinoids combined with beneficial sensorics properties.

SUMMARY OF THE INVENTION

Accordingly, there is provided a method of producing a tableted chewing gum composition for oral administration of cannabinoids, the method comprises the steps of feeding a gum composition comprising water-insoluble gum base into an extruder from one or more feeding inlets, optionally including additional ingredients, pressurizing the gum composition in the extruder while controlling temperature and pressure of the gum composition, optionally including further ingredients from one or more feeding inlets, extruding the gum composition through a die means, cutting the extruded gum composition in a liquid filled chamber, thereby obtaining a first population of particles comprising water-insoluble gum base. After this procedure, the first population of particles is included with a second population of particles comprising water-soluble chewing gum ingredients and one or more cannabinoids, the second population of particles being free of water-insoluble gum base, thereby obtaining a chewing gum composition and tableting the chewing gum composition in a tablet pressing apparatus, thereby obtaining a tableted chewing gum composition.

Several advantages are associated with the method of producing tableted cannabinoid chewing gum according to the invention in view of the prior art, both in relation to the individual method steps of the method but also in relation to the tableted chewing gum composition that is produced.

In terms of the individual method steps, one of such advantages is that extensive and costly labor work may be reduced due to the more automated method according to the invention. If large volumes of tableted chewing gum are required, these considerations may be even more pronounced as the automated process of the present invention also involves a continuous aspect that appears to be less apparent from the prior art.

Another important advantage of the present invention is that handling of the inherently sticking gum base may be improved. Partly due to the extrusion of the gum composition through a die means and cutting of this composition in a liquid filled chamber, milling may be avoided, and the gum base is less exposed to surfaces that may result in the gum base being attached to these surfaces.

The presence of a liquid filled chamber as such is also one of the advantages of the present invention. Due to the pressure of the gum composition in the extruder of the present invention, the gum composition will inherently expand due to the pressure difference upon entrance to the liquid filled chamber. Hence, when the gum composition is cut into particles, these particles will inherently be in a form of round-shaped particles with a rather smooth surface. While the particles may not be perfectly round-shaped but may have a drop-like shape to some degree due to the process, the particles may have some clear benefits according to the invention.

Turning to the milling process of the prior art involved in the production of tableted chewing gum, it is important to note that such milling inherently results in a surface of the milled particles that are less smooth compared to the particles of the present invention. In fact, milling may result in a rather coarse surface of the particles, giving a larger surface area than the particles of the present invention. Without being bound to theory, this is believed to have an impact on the resulting tableted cannabinoid chewing gum composition once the population of particles are tableted, both in relation to release properties and sensorics properties.

With respect to release properties, the present invention may offer an improved release profile of cannabinoids compared to conventional chewing gum platforms. In particular, the specific chewing gum platform of the present invention may serve to provide improved release characteristics of cannabinoids compared to conventional chewing gum platforms applied in combination with cannabinoids.

Specifically, the provision of at least two populations of particles according to the invention is beneficial in terms of delivery of cannabinoids, where a first population of particles comprises water-insoluble gum base and a second population of particles comprises water-soluble chewing gum ingredients, the second population of particles being free of water-insoluble gum base. This special construction of delivering cannabinoids provides some benefits that are not envisaged in conventional chewing gum.

In the present context, an improved release profile refer to a higher release of cannabinoids which is particularly seen as an advantage since it has traditionally been a challenge with release of cannabinoids from chewing gum. In order to obtain beneficial health effects both in terms of systemic delivery of cannabinoids as well as local delivery of cannabinoids, it is required that a certain content of cannabinoids is released over time. Hence, rapid release of cannabinoids may be an advantage of the present invention.

A very important aspect of the present invention is the provision of beneficial sensorics properties. Here, important sensorics properties include initial chew, texture, flavor perception, sweetness perception and off-notes associated with cannabinoids. These properties are both relevant from a convenience perspective in chewing gum, but certainly also in order to support an appropriate delivery of cannabinoids from chewing gum, such as an improved release profile, and avoid adverse side effects of cannabinoids.

The present inventors have shown very surprising results with the specific combination of features of the present invention in terms of these sensorics properties. It was an unexpected result that the invention could both contribute to an improved release profile, such as rapid release of cannabinoids, and at the same time provide very beneficial sensorics properties which in terms may also support an appropriate delivery of cannabinoids from chewing gum and avoid adverse side effects of cannabinoids.

One of the sensorics properties that are particularly advantageous is the initial chew. Both in order to secure a desired release of cannabinoids and to improve the sensation by a consumer, it is critical that the initial chew is improved. Also, the texture of the chewing gum during chewing is critical for the release of cannabinoids and the experience as well as convenience during chewing. These properties may be improved by the present invention which was not expected by the inventors of the present invention.

In an embodiment of the invention, at least 10% by weight of the one or more cannabinoids are present in unbound form.

A particular advantage is seen when the cannabinoids are present in unbound form. In general, the cannabinoids are present in unbound form. By "unbound form" is meant that the cannabinoids are not bound to any carrier material that limits free transfer and release of the cannabinoids in the chewing gum formulation. An example of "bound form" is if the cannabinoids are part of a plant material and the cannabinoids are not extracted and separated from the plant material. Other examples may be a pre-blend of microcrystalline cellulose which was seen by the inventors to limit free transfer of cannabinoids in the chewing gum formulation.

Also, in some embodiments, other pre-blends with water-insoluble carrier are to be avoided due to both problems with sensation appearance and release of cannabinoids.

The advantage of having the cannabinoids in free form may also be improved sensorics characteristics. For instance, plant material may compromise the chewing gum matrix and for instance microcrystalline cellulose may impact the texture of the chewing gum and the complex matrix of chewing gum in general.

Within the limits of the present invention, a certain content of cannabinoids may be present in bound form as long as a certain amount will also be present in unbound form.

In an embodiment of the invention, at least 90% by weight of the one or more cannabinoids are present in unbound form.

The advantage of having the cannabinoids in free form may also be improved sensorics characteristics. For instance, plant material may compromise the chewing gum matrix and for instance microcrystalline cellulose may impact the texture of the chewing gum and the complex matrix of chewing gum in general.

In an embodiment of the invention, the temperature of the gum composition is controlled to be above 90° C. during the pressurizing step.

In certain embodiments of the invention, the temperature is controlled to be above 90° C. during the pressurizing step. This may for instance be the case, if the flow of the gum composition through the extruder is prevented, such as if the viscosity of the gum composition is too high to give a proper flow through the extruder, or if other circumstances are imminent. In some embodiments of the invention, the gum composition is not heated through the extruder but remains at a high enough temperature through the extruder, such as if the temperature of the gum composition when feeding the extruder from one or more inlets is high enough to flow properly through the extruder. In other circumstances, the inherent heating production of the extruder when pressurizing the gum composition keeps the temperature at a level that suffice proper flow of the gum composition.

Typically, the temperature of the gum composition is around 80° C. during the pressurizing step. This would usually be adequate to keep the viscosity of the gum composition at a suitable level. However, in other embodiment the temperature may be lower or higher depending on the nature and formulation of the gum composition.

In an embodiment of the invention, the pressure of the gum composition is controlled to be of at least 5 bar during the pressurizing step.

The pressure difference of the extruder needs to be at a level where a continuous flow is achieved in the extruder and where the gum composition may be adequately extruded through the die plate. A level of at least 5 bar should be delivered. However, in some embodiments of the invention, the pressure is controlled to be above 10 bar. In some other embodiments of the invention, the pressure is controlled to be above 20 bar. In some other embodiments of the invention, the pressure is controlled to be above 30 bar. In some other embodiments of the invention, the pressure is controlled to be above 40 bar. In some other embodiments of the invention, the pressure is controlled to be above 50 bar. In some other embodiments of the invention, the pressure is controlled to be above 60 bar such as around 70 bar.

In an embodiment of the invention, the gum composition is extruded though die openings in the die means having openings of at least two different sizes to simultaneously obtain granules with different average weights.

Typically, the die plate of the invention comprise a plurality of openings, such as around 330, to allow a plurality of strings of the gum composition to be extruded into the liquid filled chamber and subsequently being transformed into particles. In some embodiments of the invention, the die plate comprise more than 50 holes. In some embodiments of the invention, the die plate comprise more than 100 holes. In some embodiments of the invention, the die plate comprise more than 150 holes. In some embodiments of the invention, the die plate comprise more than 200 holes. In some embodiments of the invention, the die plate comprise more than 300 holes. In some embodiments of the invention, the die plate comprise more than 520 holes.

Operating the extruder system may involve certain other adjustments that may give rise to various changes in the particles produced in the process. The feed rate of the extruder to the die plate may be about 250 kg/h, but may be varied according to the invention, such as from 150 to 350 kg/h, such as from 200 to 300 kg/h.

In other embodiments the extruder screw speed may be around 250 rpm but may in other embodiments be from 150 to 350 rpm, such as 200 to 300 rpm. Another adjustment is the die plate temperature, which may typically be around 170-180° C., such as from 160-190° C. The temperature of the die plate partly secures that the gum composition is smoothly delivered through the die plate and that the cutting step is adequately performer. Typically, the cutter has 8 cutting blades and operates with a speed of around 2000 rpm. However, the cutter may have a different set-up according to the invention.

The diameter of the holes of the die plate may typically be around 0.36 mm. However, holes of a different size may also be employed. Due to expansion of the gum composition through the die plate, the resulting particles will typically have an average diameter of about 1.24 mm when the hole size is 0.36 mm and the pressure difference is 71 bar. It may also be envisaged that other particle sizes may be produced by varying the parameters of the extruder. Also, when the die plate have different opening sizes, the resulting particles will have different sizes.

In an embodiment of the invention, the first population of particles, comprising water-insoluble gum base, has an average diameter in the range from 0.1 to 2.5 mm.

In an embodiment of the invention, the first population of particles, comprising water-insoluble gum base, has an average diameter in the range from 0.3 to 2.1 mm.

In an embodiment of the invention, the first population of particles, comprising water-insoluble gum base, has an average diameter in the range from 0.8 to 1.4 mm.

In an embodiment of the invention, the first population of particles includes one or more high intensity sweeteners.

The inlets of the extruder may be used to add one or more high intensity sweeteners into the gum composition during the extrusion process. By adding these components, certain benefits may be exploited for the tableted cannabinoid chewing gum composition, such as a beneficial masking of off-notes associated with the cannabinoids due to a somewhat slower release of the one or more high intensity sweeteners when introducing these in the extrusion step. These sweeteners may be introduced together with the gum composition or later in the extrusion process along the extrusion string.

In an embodiment of the invention, the first population of particles includes one or more flavoring agents.

The inlets of the extruder may be used to add one or more flavoring agents into the gum composition during the extrusion process. By adding these components, certain benefits may be exploited for the tableted cannabinoid chewing gum composition, such as a beneficial masking of off-notes associated with the cannabinoids due to a somewhat slower release of the one or more flavoring agents when introducing these in the extrusion step. These flavoring agents may be introduced together with the gum composition or later in the extrusion process along the extrusion string.

It is noted that the invention also allows for introduction of additional ingredients together with the gum composition. These ingredients may also in some embodiments comprise water-soluble chewing gum ingredients, or in some embodiments one or more cannabinoids, or tableting aids. In other embodiments, the gum composition essentially consists of gum base.

In an embodiment of the invention, the first population of particles substantially consists of water-insoluble gum base.

In an embodiment of the invention, the first population of particles is cooled in the liquid filled chamber to a temperature of 55° C. and below.

The temperature of the liquid in the liquid filled chamber, such as water, typically is around 20° C. but may be varied according to the invention. This temperature secures that the viscosity of the cut particles relatively quickly becomes high and the gum composition solidifies in the chamber. The benefit is that sticking is reduced or completely avoided.

In an embodiment of the invention, the first population of particles is cooled in the liquid filled chamber and transferred to a de-watering device.

In an embodiment of the invention, the first population of particles is dusted or coated when conveyed to the tablet pressing apparatus.

In an embodiment of the invention, the first population of particles is dusted or coated when conveyed to the tablet pressing apparatus with ingredients selected from the group consisting of magnesium stearate, calcium carbonate, talc, silica, cornstarch, sugar compounds, polyols, cellulose ethers, acrylic polymers and copolymers, sweeteners, flavors, waxes, or colours.

In an embodiment of the invention, the tablets have a weight in the range of 0.5 g to 2.5 g per tablet.

In an embodiment of the invention, the tablets have a weight in the range of 0.6 g to 2.0 g per tablet.

In an embodiment of the invention, the one or more cannabinoids are part of the water-soluble chewing gum ingredients.

In an embodiment of the invention, the one or more cannabinoids are present in the first population of particles comprising water-insoluble gum base.

In an embodiment of the invention, the one or more cannabinoids are present in the second population of particles comprising water-soluble chewing gum ingredients.

In an embodiment of the invention, the content of water-insoluble gum base of the first population of particles is more than 30% by weight of the first population of particles. In an embodiment of the invention, the content of water-insoluble gum base of the first population of particles is more than 40% by weight of the first population of particles. In an embodiment of the invention, the content of water-insoluble gum base of the first population of particles is more than 50% by weight of the first population of particles. In an embodiment of the invention, the content of water-insoluble gum base of the first population of particles is more than 70% by weight of the first population of particles. In an embodiment of the invention, the content of water-insoluble gum base of the first population of particles is more than 90% by weight of the first population of particles, such as about 100% by weight of the first population of particles.

In an embodiment of the invention, the content of water-soluble chewing gum ingredients of the second population of particles is more than 50% by weight of the second population of particles, the second population of particles being free of water-insoluble gum base.

Preferably, the water-soluble chewing gum ingredients comprise one or more sugar alcohols. In the alternative, the water-soluble chewing gum ingredients comprise one or more sugars.

In an embodiment of the invention, the content of water-soluble chewing gum ingredients of the second population of particles is more than 60% by weight of the second population of particles.

In an embodiment of the invention, the content of water-soluble chewing gum ingredients of the second population of particles is more than 70% by weight of the second population of particles.

In an embodiment of the invention, the content of water-soluble chewing gum ingredients of the second population of particles is more than 90% by weight of the second population of particles, the second population of particles being free of water-insoluble gum base.

In an embodiment of the invention, the first population of particles and the second population of particles are substantially homogeneously distributed in the tableted chewing gum composition.

Preferably, the first population of particles and the second population of particles are homogeneously distributed in the tableted chewing gum composition. This may be secured by using adequate mixing containers and avoid segregation of particles before applying the particles to the tableting apparatus. Due to potential size difference between the first population of particles and the second population of particles, the two types of particles may be mixed in a mixing container immediately before tableting is applied.

In an embodiment of the invention, the tableted chewing gum composition constitutes a plurality of particles.

Preferably, the tableted chewing gum composition substantially consists of the plurality of particles. Essentially, this means that the whole tablet is preferably made of tableted particles and an optional coating around the tablet. This was seen to provide some clear benefits with respect to release properties, delivery properties and sensorics properties.

In an embodiment of the invention, the tableted chewing gum composition comprises one or more further population of particles.

While it is preferred that two populations of particles are applied, one or more further population of particles may be applied in the present invention. For instance, a population of particles consisting of water-insoluble tableting aids, such as talc, may be applied according to the invention. In other embodiments, one or more additional population of particles containing water-soluble ingredients may be applied as well as one or more further populations of particles with a content of gum base. The aim of the annotation 'first population of particles' and 'second population of particles' is to make a distinction between particles that contain gum base and particles that do not contain gum base.

In an embodiment of the invention, the first population of particles is present in an amount of at least 15% by weight of the tableted chewing gum composition.

Generally, since the first population of particles comprise gum base, the amount of these types of particles impact the content of gum base in the tableted chewing gum. For instance, when the content of gum base is about 100% by weight of the first population of particles, the gum base content of the tableted chewing gum may be as low as 15% by weight of the tableted chewing gum composition. On the other hand, when the content of gum base is about 40% by weight of the first population of particles, the gum base content of the tableted chewing gum may also be as low as 15% by weight of the tableted chewing gum composition. In this case, the amount of the first population of particles is higher than 15% by weight of the tableted chewing gum composition.

In an embodiment of the invention, the first population of particles is present in an amount of 15 to 95% by weight of the tableted chewing gum composition.

Typically, the gum base content of the tableted chewing gum composition is higher than 15% by weight of the tableted chewing gum composition, such as about 40% by weight of the tableted chewing gum composition. In this case, the amount of the first population of particles may be 40% by weight of the tableted chewing gum composition when the gum base content in the first population of particles is about 100% by weight of the first population of particles. In another case, the amount of the first population of particles may be 80% by weight of the tableted chewing gum composition when the gum base content in the first population of particles is about 50% by weight of the first population of particles. This gives an amount of gum base of the tableted chewing gum composition of about 40% by weight of the tableted chewing gum composition.

In an embodiment of the invention, the first population of particles is present in an amount of 15 to 90% by weight of the tableted chewing gum composition. In an embodiment of the invention, the first population of particles is present in an amount of 20 to 95% by weight of the tableted chewing gum composition. In an embodiment of the invention, the first population of particles is present in an amount of 20 to 90% by weight of the tableted chewing gum composition. In an embodiment of the invention, the first population of particles is present in an amount of 20 to 80% by weight of the tableted chewing gum composition.

In an embodiment of the invention, the first population of particles is present in an amount of at least 20% by weight of the tableted chewing gum composition.

Preferably, the gum base content of the tableted chewing gum composition is about 40% by weight of the tableted chewing gum composition. In some embodiments of the invention, the amount of the first population of particles may be 40% by weight of the tableted chewing gum composition and the gum base content in the first population of particles is about 100% by weight of the first population of particles.

In some other embodiments of the invention, the amount of the first population of particles may be about 90% by weight of the tableted chewing gum composition and the gum base content in the first population of particles is about 40% by weight of the first population of particles. This gives an amount of gum base of the tableted chewing gum composition of about 36% by weight of the tableted chewing gum composition. In this case, the first population of particles may be the dominant particles of the composition, preferably containing a majority of the water-soluble ingredients of the present invention. In some embodiments of the invention, the second population of particles mainly contains flavors and auxiliary ingredients, while the water-soluble chewing gum ingredients are primarily contained in the first population of particles together with gum base.

In an embodiment of the invention, the first population of particles is present in an amount of at least 30% by weight of the tableted chewing gum composition. In an embodiment of the invention, the first population of particles is present in an amount of at least 40% by weight of the tableted chewing gum composition. In an embodiment of the invention, the first population of particles is present in an amount of at least 50% by weight of the tableted chewing gum composition. In an embodiment of the invention, the first population of particles is present in an amount of at least 70% by weight of the tableted chewing gum composition. In an embodiment of the invention, the first population of particles is present in an amount of at least 90% by weight of the tableted chewing gum composition.

In an embodiment of the invention, the first population of particles is present in an amount of 20 to 60% by weight of the tableted chewing gum composition.

While a preferred amount of gum base in the tableted chewing gum composition is about 40% by weight of the tableted chewing gum composition, the amount of gum base may be varied according to the invention.

In an embodiment of the invention, the first population of particles is present in an amount of 30 to 60% by weight of the tableted chewing gum composition. In an embodiment of the invention, the first population of particles is present in an amount of 30 to 50% by weight of the tableted chewing gum composition.

In an embodiment of the invention, the second population of particles is present in an amount of at least 40% by weight of the tableted chewing gum composition.

While the first population of particles contains gum base, the second population of particles does not contain gum base. The second population of particles may essentially consist of water-soluble ingredients, which is presently preferred. However, the second population of particles may also contain water-insoluble ingredients, such as talc, cellulose, or other water-insoluble tableting material.

In some other embodiments of the invention, the amount of the second population of particles may be about 60% by weight of the tableted chewing gum composition and the content of water-soluble ingredients in the second population of particles may be about 100% by weight of the second population of particles. This gives an amount of water-soluble ingredients of the tableted chewing gum composition of about 60% by weight of the tableted chewing gum composition. In this case, the second population of particles may be the dominant particles of the composition, preferably containing a majority of the water-soluble ingredients of the present invention.

In an embodiment of the invention, the second population of particles is present in an amount of 40 to 80% by weight of the tableted chewing gum composition. In an embodiment of the invention, the second population of particles is present in an amount of 40 to 70% by weight of the tableted chewing gum composition. In an embodiment of the invention, the second population of particles is present in an amount of 50 to 80% by weight of the tableted chewing gum composition. In an embodiment of the invention, the second population of particles is present in an amount of 50 to 70% by weight of the tableted chewing gum composition.

In an embodiment of the invention, the first population of particles is reduced in volume and cohered together resulting in a matrix of discrete areas of the tablet.

According to the invention, tableting implies that the population of particles is reduced in volume as a result of pressure applied in the tableting apparatus. Hence, while the population of particles may be free-flowing before tableting, once the particles have been pressed as part of a population of particles, and optionally additional population of particles, the volume of the particles is reduced, and the particles are cohered together into a continuous matrix, which in the present context is denoted a 'layer'.

In the present context, it is to be understood that the individual particles are not merged after tableting but remain individual 'discrete' areas after tableting, constituting the individual particles. For instance, if a particle of the first population of particles has a size of about 1 mm, the size of such a particle may be 0.9 mm after tableting and have an appearance of a discrete area cohered together randomly with particles at the outer borders of the particle, including particles of the second population of particles. Some integration of the particles may be present but generally the particles remains discrete areas of the tablet.

In an embodiment of the invention, the second population of particles is reduced in volume and cohered together resulting in a matrix of discrete areas of the tablet.

In the present context, it is to be understood that the individual particles are not merged after tableting but remain individual 'discrete' areas after tableting, constituting the individual particles. For instance, if a particle of the second population of particles has a size of about 0.1 mm, the size of such a particle may be 0.09 mm after tableting and have an appearance of a discrete area cohered together randomly with particles at the outer borders of the particle, including particles of the first population of particles.

In an embodiment of the invention, the first population of particles and the second population of particles are substantially homogeneously distributed in a first layer of the tableted chewing gum composition.

In the present context, a 'layer' is to be understood as a matrix resulting from pressing one portion of particles according to the invention. Hence, if only one portion of particles according to the invention is applied in the tableting apparatus, and this portion is pressed into a coherent tablet, this would correspond to one 'layer' or a 'first layer'. This portion may comprise one or more populations of particles. Optionally, such layer may be pressed in two steps with varying pressure. On the other hand, if another portion of particles according to the invention is applied to the tableting apparatus on top of the already pressed layer, this would correspond to another 'layer' or a 'second layer'. In the context of the invention, the second layer may also be applied in the tableting apparatus first and the first layer may be applied in the tableting apparatus in a second step. When a module of non-particulate matter is applied in the present invention, this would not be a layer in the sense of the invention. Hence, if a gel capsule is applied between two 'layers', the tableted chewing gum composition would be annotated a two-layered chewing gum composition. Likewise, with a three-layered tableted chewing gum composition.

Due to the inherent nature of conventional tablet pressing, the individual layers of a tableted composition would have a sharp line between the layers when the layers are pressed in two or more subsequent steps. This is seen from a side view of the tablet as distinct layers on top of each other. In an alternative embodiment, two or more portions are applied in subsequent steps to the tableting apparatus and pressed in one sequence. In this case there will not be a sharp line between the layers from a side view, but this would still be considered a layered tablet according to the invention, although the line between the layers would be irregular. Accordingly, in some embodiments, it is not required that layers are processed in separate tableting steps.

In an embodiment of the invention, the water-insoluble gum base is partly located in a first layer of the chewing gum composition and the water-soluble chewing gum ingredients are partly located in a second layer of the chewing gum composition.

Preferably, when a multi-layered tableted chewing gum composition is applied, it may be beneficial to partly locate the water-insoluble gum base in one layer and a part of the water-soluble chewing gum ingredients in another layer. This may both influence the release rate of the one or more cannabinoids of the composition as well as the sensorics properties of the tableted chewing gum composition.

In an embodiment of the invention, the water-insoluble gum base is located in a first layer of the chewing gum composition and the water-soluble chewing gum ingredients are partly located in a second layer of the chewing gum composition.

In one embodiment, when a multi-layered tableted chewing gum composition is applied, it may be beneficial to only locate the water-insoluble gum base in one layer, and a part of the water-soluble chewing gum ingredients in another layer or layers. This may both influence the release rate of the one or more cannabinoids of the composition as well as the sensorics properties of the tableted chewing gum composition.

In an embodiment of the invention, the water-insoluble gum base is partly located in a first layer of the chewing gum composition and partly in a second layer of the chewing gum composition.

In certain embodiments of the invention, a two-layered tableted chewing gum composition is provided with two layers comprising gum base. This configuration may be beneficial with respect to the release rate of the one or more cannabinoids of the composition as well as the sensorics properties of the tableted chewing gum composition.

In an embodiment of the invention, the water-soluble chewing gum ingredients are partly located in a first layer of the chewing gum composition and partly in a second layer of the chewing gum composition.

In an embodiment of the invention, the content of water-insoluble gum base of the first layer is more than 30% by weight of the first layer.

In an embodiment of the invention, the content of water-insoluble gum base of the first layer is more than 35% by weight of the first layer. In an embodiment of the invention, the content of water-insoluble gum base of the first layer is more than 40% by weight of the first layer.

In an embodiment of the invention, the content of water-insoluble gum base of the first layer is more than 70% by weight of the first layer.

In an embodiment of the invention, the content of water-insoluble gum base of the first layer is from 30 to 90% by weight of the first layer. In an embodiment of the invention, the content of water-insoluble gum base of the first layer is from 30 to 70% by weight of the first layer. In an embodiment of the invention, the content of water-insoluble gum base of the first layer is from 30 to 60% by weight of the first layer. In an embodiment of the invention, the content of water-insoluble gum base of the first layer is from 35 to 70% by weight of the first layer. In an embodiment of the invention, the content of water-insoluble gum base of the first layer is from 35 to 60% by weight of the first layer. In an embodiment of the invention, the content of water-insoluble gum base of the first layer is from 30 to 50% by weight of the first layer.

In an embodiment of the invention, the content of water-soluble chewing gum ingredients of the second layer is more than 50% by weight of the second layer In an embodiment of the invention, the content of water-soluble chewing gum ingredients of the second layer is more than 90% by weight of the second layer.

In an embodiment of the invention, the tableted chewing gum composition consists of two layers where a first layer is cohered to and adjacent to a second layer.

In the present context 'cohered to and adjacent to' is intended to mean that two layers are pressed together on one top side and one bottom side of two portions of particles comprising one or more populations of particles. Hence, one surface of a layer is attached to one surface of another layer, whereas additional surfaces of the portions are not exposed to each other. Seen from a side view, the layers have a tablet-slice appearance.

In an embodiment of the invention, the tableted chewing gum composition consists of three layers where one middle layer is cohered to and adjacent to two outer layers.

In the present context 'cohered to and adjacent to' is intended to mean that two outer layers are located on and attached to one top side and one bottom side of a middle layer. Seen from a side view, the layers have a tablet-slice appearance.

In an embodiment of the invention, the water-soluble chewing gum ingredients comprise one or more sugar alcohols or one or more sugars in an amount of 35-80% by weight of the tableted chewing gum composition.

In an embodiment of the invention, the water-soluble chewing gum ingredients comprise one or more sugar alcohols or one or more sugars in an amount of 40-70% by weight of the tableted chewing gum composition.

It is particularly preferred that the water-soluble chewing gum ingredients are present in an amount of 40-70% by weight of the chewing gum. This range of water-soluble chewing gum ingredients have shown particularly beneficial results. The inventors of the present invention did not expect that an improved release would be possible within this range of water-soluble chewing gum ingredients. In addition, due to the specific properties of cannabinoids, it was a surprise to discover that the release rate of cannabinoids was improved with water-soluble chewing gum ingredients.

Importantly, the sensorics characteristics were thought to be compromised when the water-soluble chewing gum ingredients are present in an amount of 40-70% by weight of the chewing gum. However, contrary to expectations, the sensorics properties were improved in combination with an improved release of cannabinoids. In particular, the texture of the chewing gum was improved. It was expected that the texture would be worse with this amount of water-soluble ingredients in the chewing gum.

In an embodiment of the invention, delivery of the one or more cannabinoids is partly controlled by means of the location of the one or more cannabinoids in the chewing gum composition.

In an embodiment of the invention, the one or more cannabinoids are located in a first layer of the chewing gum composition.

In an embodiment of the invention, the one or more cannabinoids are located in a second layer of the chewing gum composition.

In an embodiment of the invention, the one or more cannabinoids are both comprised in a first layer of the chewing gum composition and in a second layer of the chewing gum composition.

In an embodiment of the invention, delivery of the one or more cannabinoids is partly controlled by means of further release enhancing ingredients.

In an embodiment of the invention, the gum base comprising one or more natural resins in an amount of 10-40% by weight of the gum base, one or more elastomers in an amount of 3-30% by weight of the gum base, and one or more elastomer plasticizers in an amount of 8-50% by weight of the gum base.

The special combination of the present invention with one or more natural resins in a certain amount combined with one or more elastomer plasticizers in a certain amount is particularly advantageous for delivery of cannabinoids. It was unexpected to the present inventors that the combination according to the invention would contribute to improved delivery of cannabinoids. Importantly, the elastomer plasticizer in the present context serves to plasticize the elastomers present in the gum base. The elastomer plasticizers are not to be considered elastomers by themselves in the present context. The elastomeric properties are provided by the elastomers of the invention, and the elastomer plasticizers are present to plasticize the elastomers in order to obtain the beneficial delivery of the present invention.

Additionally, the specific gum base applied according to the invention further contributes to the advantages according to the invention. With respect to release properties, the present invention may offer an improved release profile of cannabinoids compared to conventional gum base. In particular, the specific gum base formulation of the present invention may serve to provide improved release characteristics of cannabinoids compared to conventional gum base applied in combination with cannabinoids.

In an embodiment of the invention, the gum base comprising one or more polyvinyl acetate elastomer plasticizers in an amount of 8-50% by weight of the gum base.

A significant advantage of the present invention is obtained when the one or more elastomer plasticizers comprise one or more polyvinyl acetate elastomer plasticizers. Surprisingly, the release characteristics of the cannabinoids were seen to be particularly improved with these elastomer plasticizers. The polyvinyl acetate elastomer plasticizers are not to be considered elastomers by themselves in the present context. Hence, the molecular weight and other polymer properties are tailored for the polyvinyl acetate elastomer plasticizers to work as plasticizers. The elastomeric properties are provided by the elastomers of the present invention and the polyvinyl acetate elastomer plasticizers are present to plasticize the elastomers in order to obtain the beneficial release characteristics of the present invention. Polyvinyl acetate elastomers are not to be considered polyvinyl acetate elastomer plasticizers.

Traditionally, water-insoluble gum base is seen as a matrix that does not offer a high degree of release of cannabinoids. In particular, with respect to cannabinoids, it is a surprise that improved release may be seen when polyvinyl acetate elastomer plasticizers are applied in the gum base.

A particularly preferred range of polyvinyl acetate elastomer plasticizers is 15-35% by weight of the gum base. Here, very advantageous results were achieved with respect to release of cannabinoids and sensorics characteristics, such as initial chew, texture, flavor perception, sweetness and off-notes. That the preferred range would be on a level such high was a surprise to the inventors. Also, it was not expected that such high amount of polyvinyl acetate elastomer plasticizers would have a combined effect of improved sensorics properties.

In other embodiments of the invention, the one or more polyvinyl acetate elastomer plasticizers are present in an amount of 17-33% by weight of the gum base. In other embodiments of the invention, the one or more polyvinyl acetate elastomer plasticizers are present in an amount of 20-35% by weight of the gum base. In other embodiments of the invention, the one or more polyvinyl acetate elastomer plasticizers are present in an amount of 20-30% by weight of the gum base. In other embodiments of the invention, the one or more polyvinyl acetate elastomer plasticizers are present in an amount of 15-40% by weight of the gum base. In other embodiments of the invention, the one or more polyvinyl acetate elastomer plasticizers are present in an amount of 20-40% by weight of the gum base.

In an embodiment of the invention, the water-insoluble gum base is a natural gum base comprising natural ingredients, such as chicle.

In an embodiment of the invention, the gum base comprises less than 50% by weight of gum base polymers.

In order to achieve the effects of the invention, it may in some embodiments be preferred that the content of polymers is relatively low. This ensures for instance that the release of cannabinoids may be improved and that the sensorics properties of the chewing gum may be improved. In particular, when vinyl laurate-vinyl acetate copolymers are applied, it appears critical that the content of gum base polymers should be below 50% by weight of the gum base. It appears that this polymer may compromise the chewing gum formulation in the present context.

In an embodiment of the invention, the gum base does not comprise vinyl laurate-vinyl acetate copolymer.

To the surprise of the inventors, it was seen that vinyl laurate-vinyl acetate copolymer may compromise the release of cannabinoids and the sensorics characteristics of the chewing gum. Hence, it is preferred that this copolymer is not present in the gum base.

In certain other embodiments, the gum base polymers comprise less than 20% by weight of vinyl laurate-vinyl acetate copolymer. In certain other embodiments, the gum base polymers comprise less than 15% by weight of vinyl laurate-vinyl acetate copolymer. In certain other embodiments, the gum base polymers comprise less than 10% by weight of vinyl laurate-vinyl acetate copolymer. In certain other embodiments, the gum base polymers comprise less than 5% by weight of vinyl laurate-vinyl acetate copolymer.

In some embodiments of the invention, if polyvinyl acetate elastomers are present in the gum base formulation, the gum base polymers comprise less than 20% by weight of vinyl laurate-vinyl acetate copolymer, such as less than 10%, such as less than 5%. In the present context, polyvinyl acetate elastomers are not the same as polyvinyl acetate elastomer plasticizers. Basically, polyvinyl acetate elastomers provides elastomeric properties to the chewing gum, whereas polyvinyl acetate elastomer plasticizers work to plasticize the elastomers present in the gum base.

In an embodiment of the invention, the gum base comprising one or more natural resins in an amount of 15-35% by weight of the gum base.

The natural resins provides beneficial properties to the present invention. In particular the combination of natural resins and elastomer plasticizers provides beneficial properties to the gum base and followingly to the chewing gum formulation in general, both in terms of release properties of cannabinoids and sensorics properties.

A particularly advantageous range of natural resins is 15-35% by weight of the gum base. This range of natural resin was seen to give an improved release profile and best sensorics properties. While natural resins of 10-40% by weight of gum base is also within the scope of the invention, the best results were seen with 15-35% by weight of the gum base.

In other embodiments of the invention, the one or more natural resins are present in an amount of 17-33% by weight of the gum base. In other embodiments of the invention, the one or more natural resins are present in an amount of 20-35% by weight of the gum base. In other embodiments of the invention, the one or more natural resins are present in an amount of 20-30% by weight of the gum base. In other embodiments of the invention, the one or more natural resins are present in an amount of 15-40% by weight of the gum base. In other embodiments of the invention, the one or more natural resins are present in an amount of 20-40% by weight of the gum base.

In an embodiment of the invention, the gum base comprising one or more natural resins selected from the group consisting of polyterpene resins, resins based on gum rosin, wood rosin or tall oil resin.

In an embodiment of the invention, the gum base comprising one or more elastomers selected from the group consisting of styrene-butadiene copolymers, polyisobutylene, isobutylene-isoprene copolymers, polyethylene, polyurethane or any combination thereof.

In an embodiment of the invention, the one or more elastomers are present in an amount of 3-20% by weight, such as in an amount of 3-15% by weight, such as in an amount of 5-10% by weight.

In an embodiment of the invention, the amount of gum base in the chewing gum composition is 15-60% by weight of the tableted chewing gum composition.

In an embodiment of the invention, the release rate of the one or more cannabinoids is at least 20% by weight of the one or more cannabinoids within the first 5 minutes upon oral administration.

In certain product formulations, such as formulations where systemic effects are to be achieved relatively quickly, it is advantageous that the release profile is high. In the present context, a release rate of more than 20% is considered to be relatively high. Due to the specific properties of cannabinoids, a release rate of more than 20% is considered to be high. The inventors of the present invention did not expect that such a release rate could be obtained according to the invention. It was expected that the specific composition of the gum base would not allow such a high release rate.

In an embodiment of the invention, the release rate of the one or more cannabinoids is at least 30% by weight of the one or more cannabinoids within the first 5 minutes upon oral administration.

In certain embodiments of the invention, the release rate is higher than 30% within the first 5 minutes upon oral administration. In this context the release rate is measured from the time that the chewing gum is inserted in the mouth and the initial chew is effectuated and chewing is commenced with a suitable chewing gum rate, such as 1 chew pr. second, until 5 minutes of chewing.

Importantly, the improved sensorics characteristics of the chewing gum of the invention also accommodates an improved release rate of cannabinoids. The reason may be attributed to the fact that if the initial chew is improved and the chewing gum texture is also improved, this would trigger the user to effectively chew the product. Also, the production of saliva may be enhanced once the product formulation is improved, which in turn may accommodate further increased release of cannabinoids. However, the precise mechanism is not well understood.

In an embodiment of the invention, the one or more cannabinoids are not part of a pre-mixture with microcrystalline cellulose.

In the present context, a premixture is mainly used to allocate the one or more cannabinoids properly to the manufacturing process and secure that the uniformity is not compromised and that the cannabinoids are distributed properly into the mixture. Preferably, the cannabinoids are provided in a premixture with one or more sugar alcohols. It was a surprise to the inventors that a premixture was important to have the cannabinoids distributed properly in the manufacturing process and to end up with a product where the uniformity was consistent.

In an embodiment of the invention, the one or more cannabinoids are present in an amount of 0.1 to 200 mg. In some other embodiments of the invention, the one or more cannabinoids are present in an amount of 0.1 to 100 mg. In some other embodiments of the invention, the one or more cannabinoids are present in an amount of 0.1 to 50 mg. In an embodiment of the invention said chewing gum comprises said cannabinoids in an amount of 0.1-30 mg, such as 1-20 mg, such as 5-15 mg.

In an embodiment of the invention, the one or more cannabinoids comprise cannabidiol (CBD), cannabidiolic acid (CBDA), cannabidivarin (CBDV), salts and derivatives thereof. In an embodiment of the invention the one or more cannabinoids comprises CBD, salts and derivatives thereof, including analogues and homologues. In an embodiment of the invention said one or more cannabinoids comprises CBD. In an embodiment of the invention said one or more cannabinoids is CBD.

In an embodiment of the invention, the one or more cannabinoids comprise tetrahydrocannabinol (THC), tetrahydrocannabinolic acid (THCA), tetrahydrocannabivarin (THCV), salts and derivatives thereof. In an embodiment of the invention said one or more cannabinoids comprises tetrahydrocannabinol (THC). Preferably THC is intended to mean $(-)$-trans-$\Delta^9$-tetrahydrocannabinol, i.e. (6aR,10aR)-delta-9-tetrahydrocannabinol). In an embodiment of the invention said one or more cannabinoids is THC.

In an embodiment of the invention, the one or more cannabinoids comprise cannabigerol (CBG), salts and derivatives thereof.

In an embodiment of the invention, the one or more cannabinoids comprise at least two cannabinoids. In an embodiment of the invention said one or more cannabinoids comprises a combination of several cannabinoids, such as THC and CBD. In an embodiment of the invention said one or more cannabinoids is a combination of THC and CBD.

In an embodiment of the invention the chewing gum comprises gum base in an amount of 30-75% by weight of the chewing gum before any optionally applied coating, such as 35-70% by weight of the chewing gum or 40-65% by weight of the chewing gum or 45-60% by weight of the chewing gum.

In an embodiment of the invention the chewing gum comprises wax. In an embodiment of the invention the chewing gum comprises fat.

In an embodiment of the invention the chewing gum comprises flavor in an amount between 0.01 and 10% by weight of the chewing gum such as in an amount between 0.01 and 5% by weight of the chewing gum.

According to an advantageous embodiment of the invention, the chewing gum may be formulated with flavors, e.g. flavors including acids, which may be more acceptable for seriously ill patients, such as patients receiving chemotherapy.

In an embodiment of the invention the chewing gum comprises high intensity sweetener.

In an embodiment of the invention, the one or more cannabinoids are present in solid form. In an embodiment of the invention, the one or more cannabinoids are present in liquid or semi-liquid form. In an embodiment of the invention, the one or more cannabinoids are present in granules.

In an embodiment of the invention, the one or more cannabinoids are present in a pre-mixture with one or more sugar alcohols or one or more sugars.

In the present context, a pre-mixture is mainly used to allocate the one or more cannabinoids properly to the manufacturing process and secure that the uniformity is not compromised and that the cannabinoids are distributed properly into the mixture. Preferably, the cannabinoids are provided in a premixture with one or more sugar alcohols. It was a surprise to the inventors that a premixture was important to have the cannabinoids distributed properly in the manufacturing process and to end up with a product where the uniformity was consistent.

In an embodiment of the invention, the one or more cannabinoids form part of a complex with cyclodextrin. This complex may enhance the release of cannabinoids according to the present invention.

In an embodiment of the invention, the one or more cannabinoids comprise at least one phytocannabinoid that forms part of an extract. In some embodiments of the invention, it was seen that cannabinoids as part of an extract may enhance the release of cannabinoids. It was also seen that the lower concentration applied in the extract, the higher release.

In an embodiment of the invention, the chewing gum further comprising terpenes, such as at least one terpene that forms part of an extract.

In an embodiment of the invention, the one or more cannabinoids comprise at least one isolated cannabinoid.

In an embodiment of the invention, the one or more cannabinoids comprise at least one water-soluble cannabinoid. Water-soluble cannabinoids may enhance the release according to the present invention.

In an embodiment of the invention, the chewing gum comprises one or more emulsifiers.

In an embodiment of the invention the chewing gum comprises emulsifiers in an amount of 0.1% to 25% by weight of said chewing gum, such as 1-10% by weight of said chewing gum, such as 2-8% by weight of said chewing gum.

In an embodiment of the invention the emulsifiers are selected from the group of acetylated monoglycerides, mono- and/or di-glycerides of fatty acids such as glycerol monostearate, acetem, lecithin and any combination thereof.

In an embodiment of the invention, the chewing gum comprises one or more solubilizers.

In an embodiment of the invention, the chewing gum comprises a self-emulsifying agent.

In an embodiment of the invention, the chewing gum comprises a polymer carrier for the one or more cannabinoids.

In an embodiment of the invention, the chewing gum comprises a lipid carrier for the one or more cannabinoids.

In an embodiment of the invention, the chewing gum comprises enzyme inhibitors.

In an embodiment of the invention, the chewing gum comprises one or more antioxidants.

In an embodiment of the invention, the one or more cannabinoids have a systemic effect.

In an embodiment of the invention, the one or more cannabinoids have a local effect.

In an embodiment of the invention, the one or more cannabinoids are comprised in an outer coating of the chewing gum.

In certain embodiments of the invention, the cannabinoids are present in the coating of the chewing gum. This is particularly preferred when an enhanced release of cannabinoids are preferred. Also, if controlled release of cannabinoids is preferred, it is an advantage to partly allocate cannabinoids in the coating. It was not expected by the inventors of the present invention that it was possible to use a coating to deliver cannabinoids. By combining cannabinoids in the coating and in the chewing gum, controlled release of cannabinoids may be provided. In the present context, cannabinoids may both be allocated in the coating, in the chewing gum or in both places.

In an embodiment of the invention, the tableted chewing gum composition comprises one or more modules that do not comprise particles.

In the present context, a 'module' is to be understood as a matrix of non-particulate matter, cohered together with the tableted particles of the present invention. A 'module' may for instance be a sheet of conventional extruded chewing gum that is applied during the tableting process, such as after a first pressing step in the tableting apparatus where the sheet is applied and optionally pressed on top of the already pressed tablet. In other embodiments, the extruded sheet may be applied in other configurations with the tableted particles of the invention.

Another option is to apply a non-particulate capsule, such as a gel capsule, and pressing this capsule together with the particles of the invention. This may be done by pressing a first portion of particles and subsequently locate the gel capsule centrally in a cavity of the pressed material after which another portion of particles is pressed on top of the capsule, fully enclosing the capsule after the second pressing step. Another option is to have relatively small gel capsules mixed with the particles of the invention and pressing the capsules together with the whole mixture in one or more steps. However, an important aspect of the invention is that the main part of the tableted chewing gum composition originates from particulate material.

When a module of non-particulate matter is applied in the present invention, this would not be a layer in the sense of the invention. Hence, if a gel capsule is applied between two 'layers', the tableted chewing gum composition would be annotated a two-layered chewing gum composition. Likewise, with a three-layered tableted chewing gum composition.

In another aspect of the invention, there is provided an intermediate chewing gum product for oral administration of cannabinoids, the product comprising the chewing gum composition of the first aspect of the invention as described on the previous pages. Importantly, this product may comprise the particulate material according to the invention before tableting. Also, the product may constitute the particulate material according to the invention.

In another aspect of the invention, there is provided a tableted chewing gum composition for oral administration of cannabinoids, the tableted chewing gum composition comprising the chewing gum composition of the first aspect of the invention as described on the previous pages.

In another aspect of the invention, the chewing gum of the present invention may be used for the treatment or alleviation of a medical condition.

In certain embodiments of the invention, the chewing gum of the present invention may be used for the treatment or alleviation of a medical condition selected from the group consisting of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In the present context, the chewing gum of the invention may be applied for the medical indications as single indications from the list of indications. The invention may also be applied for other medical indications and indications that are not medical for instance local conditions in the mouth that may be treated or alleviated with the formulation of the present invention. The list is not exhaustive and other indications are part of the present invention.

In another aspect of the invention, a package is provided comprising a chewing gum according to the invention, the package comprising a material acting as a barrier for the one or more cannabinoids and oxygen, preferably a copolymer of acrylonitrile and methyl acrylate.

In certain embodiments of the invention, the package includes a liquid or a semisolid for the provision of a preventive environment therein.

In certain embodiments of the invention, the package comprising a chewing gum according to the invention, wherein the package is a blister package.

FIGURES

FIGS. 1a and 1b illustrates a tableted chewing gum composition with one layer,

FIGS. 2a and 2b illustrates a tableted chewing gum composition with two layers,

FIGS. 3a and 3b illustrates a tableted chewing gum composition with three layers.

Figure 4:
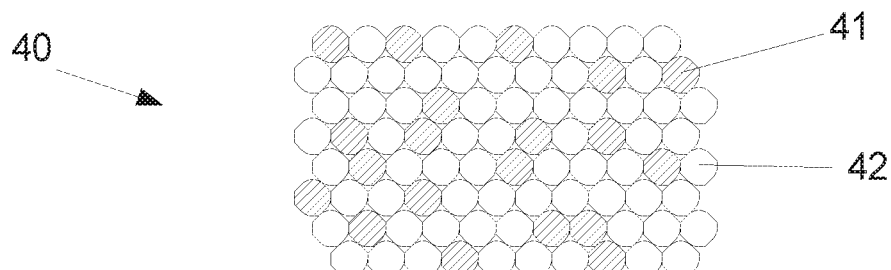
FIGS. 4 and 5 illustrates a first and a second population of particles.

The invention will now be described in more details with reference to FIG. 1-6. These illustrations are intended to be understood in connection with the rest of the description, including the Summary of the Invention, the Detailed Description and the Examples of the invention.

FIG. 1a and FIG. 1b illustrates an embodiment of a tableted chewing gum composition 10 with a first layer 11. FIG. 1a is a cross-section of the tableted chewing gum composition and FIG. 1b illustrates the tableted chewing gum composition seen from above. The tablet comprises an upper surface and a bottom surface as well as a circular side surface.

FIG. 2a and FIG. 2b illustrates an embodiment of a tableted chewing gum composition 20 with two layers 21,22. FIG. 2a illustrates a cross-section of the tableted chewing gum composition and FIG. 2b illustrates the tableted chewing gum composition seen from above. The tablet comprises an upper surface and a bottom surface as well as a circular side surface. The tablet comprises a first layer 21 and a second layer 22.

FIG. 3a and FIG. 3b illustrates an embodiment of a tableted chewing gum composition 30 with three layers 31,32,33. FIG. 3a illustrates a cross-section of the tableted chewing gum composition and FIG. 3b illustrates the tableted chewing gum composition seen from above. The tablet comprises an upper surface and a bottom surface as well as a circular side surface. The tablet comprises a first layer 33 and a second layer 31 and a third layer 32.

FIG. 4 illustrates a closer view 40 of a cross-section of the first layer 11,21,33 of the tableted chewing gum compositions according to FIG. 1a-3a. In this embodiment, a first population of particles 41 is homogeneously distributed with a second population of particles 42 according to the invention. In this example the first and second population of particles are similar in size. The gum base content is illustrated with shadings of the first population of particles 41.

Figure 5:
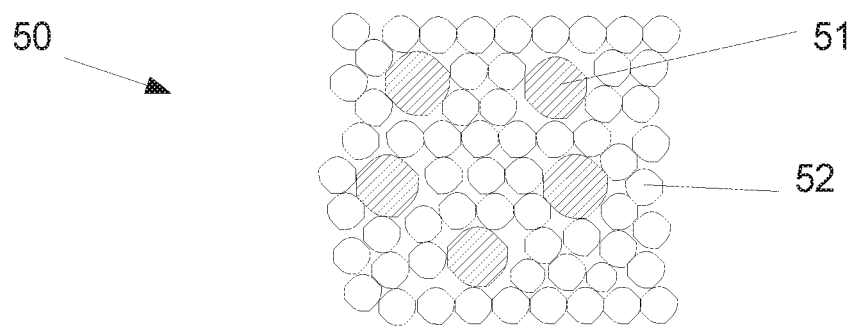

FIG. 5 illustrates a closer view 50 of a cross-section of the first layer 11,21,33 of the tableted chewing gum compositions according to FIG. 1a-3a. In this embodiment, a first population of particles 51 is homogeneously distributed with a second population of particles 52 according to the invention. In this example the particles of the first population of particles are larger in size than the particles of the second population of particles. The gum base content is illustrated with shadings of the first population of particles 51.

Figure 6:
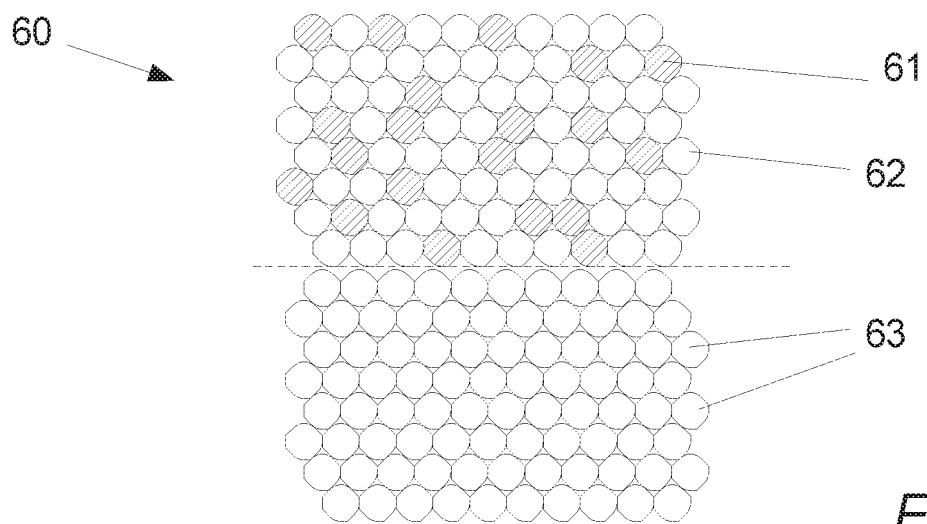
FIG. 6 illustrates a first and a second population of particles in a tableted chewing gum composition with two layers.

FIG. 6 illustrates a closer view 60 of a cross-section of the tableted chewing gum compositions according to FIGS. 2a and 3a in the intersection between the individual layers 21,22 and 33,32. In this embodiment, a first population of particles 61 is homogeneously distributed with a second population of particles 62 in layer 21,33 whereas a second population of particles 63 is present in layer 22,32 without presence of the first population of particles. The gum base content is illustrated with shadings of the first population of particles 61.

DETAILED DESCRIPTION OF THE INVENTION

The invention will now be described in more details with respect to certain aspects and embodiments of the invention. These aspects and embodiments are intended to be understood in connection with the rest of the description, including the Summary of the Invention, the Figures and the Examples of the invention.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in connection with the word comprising or containing denote "one or more." The expression "one or more" is intended to mean one, two, three or more.

In the present context the phrase "first population of particles", "second population of particles" or "further populations of particles" refer to a distinct population of particles. The expression "first", "second" or "third" is intended to mean that the individual populations have different compositions, e.g. a "first" population may be a portion of particles that have a content of gum base whereas a "second" population may be a portion of particles that does not have a content of gum base. However, if a "first" and "second" population is applied in one layer of a tablet, a "first" population in a second layer of the tablet may also have a different composition compared to a "first" population in the first layer. This may for instance be the case when one type of sugar alcohol is applied as a "first population of particles" in one layer and another type of sugar alcohol is applied as a "first population of particles" in another layer. The intention with the wording is mainly to distinguish two or more populations that are applied together, for instance in a homogeneous mixture. The individual particles in a "population" may comprise more than one ingredient, such as for instance both water-insoluble gum base and water-soluble chewing gum ingredients, or other ingredients.

The term "population" as such is intended to mean a statistical population of particles characterized by a number of different parameters, e.g. statistical parameters such as distribution of particles, average particle size, particle size distribution width, etc. Hence, a "population" may be a portion of particles characterized by having a normal distribution of particles with an average particle size, mean particles size and a distribution width. However, a "population" may also be a portion of particles that have undergone sieving where a certain lower or upper limit of particles size is present which does not necessarily give a normal distribution of particles.

The term "particle size" relates to the ability of the particles to move through or be retained by sieve holes of a specific size. The content of particles having a particle size in a certain size range is provided as weight percent relative to the total weight of the particle population in question. For instance, the population of particles having a content of gum base may e.g. comprise 40% (w/w) particles having a size in the range of 500-800 microns and 60% (w/w) particles having a size in the range of 800-1400 microns. An average "particles size" is intended to mean a statistical average.

The term "plurality of particles" is intended to cover the "population of particles" in the sense that the sum of populations are covered by the term "plurality".

The term "portion of particles" or similar wording is intended to mean a plurality of particles that collectively may comprise one or more populations of particles. For instance, a "portion of particles" may be applied in a tableting apparatus and pressed into a first layer of a tableted chewing gum composition. This layer may comprise one population of particles or a "first population of particles". However, this portion may also comprise two "populations of particles", etc.

The term "particle" or similar wording is intended to denote a single, discrete composition of solid matter, such as a granule or individual elements in powder, having a certain size that may deviate considerable.

By the terms "water-insoluble gum base" or "gum base" or "gum base matrix" or similar wording is meant the mainly water-insoluble ingredients and hydrophobic gum base ingredients.

The "gum base" may contain gum base polymers and plasticizers, waxes, emulsifiers, fats and/or fillers.

The term "water-soluble chewing gum ingredients" intends to mean the mainly water-soluble and hydrophilic chewing gum ingredients.

The term "tableted" is intended to mean that the chewing gum composition is pressed in a tableting apparatus and mainly being composed of particulate matter, such as one or more populations of particles or plurality of particles. Although the term "tableted" implies a method step, in the present context, the term is intended to mean the resulting tablet obtained in tableting a portion of particles. It is noted that a tablet or tableted composition that is mentioned to comprise particles eventually is to be understood as particles that have been pressed together in a tableting step.

The term "weight of the chewing gum" or similar wording meaning the same is defined in the present context as weight of the chewing gum, not including the weight of an outer coating, such as a hard coating, soft coating, and the like.

By the phrase "texture" is meant a qualitative measure of the viscoelastic properties of the chewing gum and of the overall mouth-feel experienced by the user during the chewing process. Thus, the term "texture" encompasses measurable quantities such as hardness and elasticity as well as more subjective parameters related to the chew-feel experienced by a user.

The term "in vivo chewing" intends to mean that the chewing gum system is chewed by a human subject in an experimental setup of trained test persons according to statistically principles and that either the saliva of the human subject is subject to measurements or the chewed chewing gum is subject to measurements, the experimental setup being performed at a chewing frequency of 60 chews per minute.

The term "in vivo release" or "in vivo testing of release" or similar wording intends to mean that the chewing gum is tested according to Example 24.

The term "in vitro release" or "in vitro testing of release" or similar wording intends to mean that the chewing gum is tested according to Example 25, in particular according to Dissolution Test for Chewing Gums, General Monograph 2.9.25 in European Pharmacopoeia, 5th ed.

The term "release" in the present context is intended to mean under "in vitro" conditions if not stated otherwise. In particular, the "release rate" during a certain period of time is intended to mean the amount in percentage of cannabinoids that is released during the period at a chewing frequency of 60 chews per minute.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from a gum by the aid of active chewing of the gum in the oral cavity of the subject, whereby the active chewing is controlling the amount of substance released.

The term "delivery to the oral mucosa" or similar wording intends to mean that the chewing gum is tested according to Example 27.

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion.

The term "natural resin", as used herein, means resinous compounds being either polyterpene derived from terpenes of natural origin or resinous compounds derived from gum rosin, wood rosin or tall-oil rosin.

The gum base is the masticatory substance of the chewing gum, which imparts the chew characteristics to the final product. The gum base typically defines the release profile and plays a significant role in the gum product. The gum base portion is retained in the mouth throughout the chew. The water-soluble portion disappears over a period of time during chewing.

According to embodiments of the invention, a preferred amount of gum base matrix in the final chewing gum is 30-75% by weight of the chewing gum before any optionally applied coating, such as 35-70% by weight of the chewing gum or 40-65% by weight of the chewing gum or 45-60% by weight of the chewing gum.

Elastomers provide the rubbery, elastomeric and bouncing nature to the gum, which varies depending on this ingredient's chemical structure and how it may be compounded with other ingredients. Elastomers suitable for use in the gum base and gum of the present invention may include natural or synthetic types. Polyvinyl acetate elastomer plasticizers are not considered elastomers according to the invention.

Elastomers may be selected from the group consisting of styrene-butadiene copolymers, polyisobutylene, isobutylene-isoprene copolymers, polyethylene, polyurethane or any combination thereof. Preferred elastomers are styrene-butadiene copolymers (SBR), polyisobutylene and isobutylene-isoprene copolymers (BR).

Styrene-butadiene type elastomers, or SBR as they may be called, typically are copolymers of from about 20:80 to 60:40 styrenes:butadiene monomers. The ratio of these monomers affects the elasticity of the SBR as evaluated by mooney viscosity. As the styrene:butadiene ratio decreases, the mooney viscosity decreases.

The structure of SBR typically consists of straight chain 1,3-butadiene copolymerized with phenylethylene (styrene). The average molecular weight of SBR is <600,000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene). The average molecular weight of BR is in the range from 150,000 g/mole to 1,000,000 g/mole.

Polyisobutylene, or PIB as they may be called, type elastomers are polymers of 2-methylpropene. The low molecular weight elastomers provide soft chew characteristics to the gum base and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high molecular weight elastomers provide elasticity to the gum. Average molecular weight may range from 120,000 to 1,000,000 g/mole.

Polybutene range in average molecular weight from about 5.000 g/mole to about 30.000 g/mole.

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang. Natural elastomers may also be applied in aspects of the present invention.

Elastomer plasticizers vary the firmness of the gum base. Their specificity on elastomer inter-molecular chain breaking (plasticizing) along with their varying softening points cause varying degrees of finished gum firmness and compatibility when used in base. Polyvinyl acetate elastomers plasticizers are examples of elastomer plasticizers of the present invention.

In some embodiments of the invention, the weight-average molecular weight (Mw) of the one or more polyvinyl acetate elastomer plasticizers is from 5,000 to 40,000. In some embodiments of the invention, the weight-average molecular weight (Mw) of the one or more polyvinyl acetate elastomer plasticizers is from 6,000 to 35,000. In some embodiments of the invention, the weight-average molecular weight (Mw) of the one or more polyvinyl acetate elastomer plasticizers is from 7,000 to 30,000. In some embodiments of the invention, the weight-average molecular weight (Mw) of the one or more polyvinyl acetate elastomer plasticizers is from 8,000 to 25,000. In some embodiments of the invention, the weight-average molecular weight (Mw) of the one or more polyvinyl acetate elastomer plasticizers is from 10,000 to 20,000.

In some embodiments of the invention, the viscosity of the one or more polyvinyl acetate elastomer plasticizers is from 1.0 to 3.0 mPa*s as measured according to ASTM D445-06 (10 wt. % in ethyl acetate), such as from 1.0 to 2.5 mPa*s.

In some embodiments of the invention, the K value of the one or more polyvinyl acetate elastomer plasticizers is from 15 to 33 as measured according to DIN 53726 (1 wt. % in acetone), such as from 18 to 30.

Generally, the term "polyvinyl acetate elastomer plasticizer" is intended to mean polyvinyl acetate having a weight-average molecular weight (Mw) of less than about 40,000.

Generally, the term "polyvinyl acetate elastomer" is intended to mean polyvinyl acetate having a weight-average molecular weight (Mw) of more than about 40,000.

In certain embodiments of the invention, the gum base comprises less than 10% by weight of polyvinyl acetate elastomer. In certain embodiments of the invention, the gum base comprises less than 5% by weight of polyvinyl acetate elastomer. In certain embodiments of the invention, the gum base comprises 2 to 6% by weight of polyvinyl acetate elastomer. In certain embodiments of the invention, the gum base comprises 3 to 5% by weight of polyvinyl acetate elastomer. In certain embodiments of the invention, the gum base is substantially free of polyvinyl acetate elastomer.

In certain embodiments of the invention, the gum base comprises 15-35% by weight of the one or more polyvinyl acetate elastomer plasticizers and less than 10% by weight of polyvinyl acetate elastomer. In certain embodiments of the invention, the gum base comprises 15-35% by weight of the one or more polyvinyl acetate elastomer plasticizers and less than 5% by weight of polyvinyl acetate elastomer. In certain embodiments of the invention, the gum base comprises 15-35% by weight of the one or more polyvinyl acetate elastomer plasticizers and 2 to 6% by weight of polyvinyl acetate elastomer.

Natural resins may be selected from ester gums including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the chewing gum comprises further chewing gum ingredients selected from the group consisting of flavors, dry-binders, tableting aids, anti-caking agents, emulsifiers, antioxidants, enhancers, mucoadhesives, absorption enhancers, high intensity sweeteners, softeners, colors, active ingredients, water-soluble indigestible polysaccharides, water-insoluble polysaccharides or any combination thereof.

According to embodiments of the invention, the emulsifiers may be selected from the group consisting of sucrose ester of fatty acids (such as sucrose mono stearate), polyethylene glycol esters or ethers (PEG) (such as caprylocaproyl macrogol-8 glycerides and lauroyl macrogol-32-glycerides), mono- and diglyceride of fatty acids (such as glycerol monostearate, glycerol monolaurate, glyceryl behenate ester), acetic acid esters of mono- and diglycerides of fatty acids (Acetem), polyoxyethylene alkyl ethers, diacetyl tartaric ester of monoglycerides, lactylated monoglycerides, glycerophospholipids (such as lecithin), poloxamer (non-ionic block copolymer of ethylene oxide and propylene oxide), cyclodextrins, fatty acid esters of sorbitol (such as sorbitan monolaurate, sorbitan monostearate, sorbitan tristearate, polysorbates). Self-emulsifying emulsifiers may be phospholipids (Lecithin), Polysorbates (polysorbate 80).

SEDDS (self-emulsifying drug delivery system) may consist of hard or soft capsules filled with a liquid or a gel that consists of self-emulsifiers, one or more cannabinoids, oil (to dissolve the cannabinoids) and a surfactant. SEDDS may comprise of a blend or mixture of self-emulsifiers, one or more cannabinoids, oil (to dissolve the cannabinoids) and a surfactant. SEDDS may comprise granules comprising self-emulsifiers, one or more cannabinoids, oil (to dissolve the cannabinoids) and a surfactant. Upon contact with gastric fluid, the SEDDS spontaneously emulsify due to the presence of surfactants. Many surfactants, however, are lipid based and interact with lipases in the GIT (gastro intestinal tract). This can lead to a reduced capability of the lipid-based surfactants to emulsify the one or more cannabinoids as well as the oil carrier, both reducing bioavailability.

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C (ascorbic acid or corresponding salts (ascorbates)), propyl gallate, catechins, other synthetic and natural types or mixtures thereof.

Further chewing gum ingredients, which may be included in the chewing gum according to the present invention, include surfactants and/or solubilizers. As examples of types of surfactants to be used as solubilizers in a chewing gum composition according to the invention, reference is made to H. P. Fiedler, Lexikon der Hilfstoffe für Pharmacie, Kosmetik und Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilizers are polyoxyethylene stearates, such as for instance poly-oxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block-copolymers of ethylene oxide and propyleneoxide and polyoxyethylene fatty alcohol ether. The solubilizer may either be a single compound or a combination of several compounds. In the presence of an active ingredient, such as the included one or more cannabinoids, the chewing gum may preferably also comprise a carrier known in the arts of chewing gum and active ingredients. Poloxamer F68 is a further highly suitable solubilizer.

High intensity artificial sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the high-intensity sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated high-intensity sweetener will be proportionately higher.

A chewing gum and/or gum base may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof. According to an embodiment of the invention, one preferred filler/texturizer is calcium carbonate.

A number of chewing gum components well known within the art may be applied within the scope of the present invention. Such components comprise but are not limited to waxes, fats, softeners, fillers, bulk sweeteners, flavors, antioxidants, emulsifiers, coloring agents, binding agents and acidulants.

In an embodiment of the invention, water-soluble ingredients comprise at least one sugar alcohol. The at least one sugar alcohol may be selected from the group consisting of xylitol, sorbitol, mannitol, maltitol, isomaltitol, isomalt, erythritol, lactitol, maltodextrin, hydrogenated starch hydrolysates, and combinations thereof.

A specific example of one category of polyol sweeteners include sugars, in particular a sugar selected from the group consisting of dextrose, sucrose, maltose, fructose, lactose, and combinations thereof.

A method of manufacturing tableted chewing gum according to the invention may be as follows: Gum bases are typically prepared by adding an amount of the elastomer, elastomer plasticizer and filler to a heated (100° C.-120° C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixing kettle in order to attain a proper consistency and by the degree of compounding desired to break down the elastomer and increase chain branching. The higher the level of filler at the start or selection of a filler having a certain particle size distribution, the higher the degree of compounding and thus more of the elastomeric chain crosslinking are broken, causing more branching of the elastomer thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and compounded for the time desired, the balance of the gum base ingredients are added in a sequential manner until a completely homogeneous molten mass is attained. Typically, any remainder of elastomer, elastomer plasticizer and filler, are added within 60 minutes after the initial compounding time. The filler and the elastomer plasticizer would typically be individually weighed and added in portions during this time. The optional waxes, softeners and antioxidants are typically added after the elastomer and elastomer plasticizers and during the next 60 minutes. Then the mass is allowed to become homogeneous before dumping.

Typical gum base processing times may vary from about one to about three hours, preferably from about 1½ to 2½ hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above described procedure may be followed.

The gum base (or gum composition) may be further processed in an extruder where the gum composition is extruded through a die plate into a liquid filled chamber, resulting in particles directly applicable for tableting. Alternatively, the gum base may be milled into a desired particle range.

The water-soluble chewing gum ingredients of the tableted chewing gum may comprise softeners, sweeteners, high intensity sweeteners, flavoring agents, acidulants, fillers, antioxidants, and other components that provide desired attributes. Softeners typically constitute from about 0.5% to about 25.0% by weight of the chewing gum. The bulking agents generally comprise from about 5% to about 90%, preferably from about 20% to about 80% of the chewing gum. High-intensity sweeteners in gum typically may range from about 0.01 to 0.50 weight percent. Flavoring agents may be present in the chewing gum in an amount within the range of from about 0.1 to about 15.0 weight percent of the gum.

The water-soluble chewing gum ingredients of the tableted chewing gum composition according to the invention may be part of the first population of particles and subsequently subject to further processing in an extruder where the gum composition is extruded through a die plate into a liquid filled chamber, before tableting. However, the water-soluble chewing gum ingredients may also be part of a second population of particles or further populations of particles that are not exposed to a liquid filled chamber but applied together with the first population of particles to a tableting apparatus. In yet another embodiments, the water-soluble chewing gum ingredients may be part of the particles comprising water-insoluble gum base and not exposed to a liquid filled chamber but used directly in a tableting apparatus, optionally together with additional separate ingredients.

In an embodiment of the invention, the first population of particles, comprising water-insoluble gum base, has an average diameter in the range from 0.1 to 2.5 mm.

In an embodiment of the invention, the first population of particles, comprising water-insoluble gum base, has an average diameter in the range from 0.3 to 2.1 mm.

In an embodiment of the invention, the first population of particles, comprising water-insoluble gum base, has an average diameter in the range from 0.8 to 1.4 mm.

The tableted chewing gum composition according to the invention is manufactured by applying pressure to a content of particles by suitable compression means. The particles or powder is then pressed into a compact coherent tablet. The particles may for example comprise so-called primary particles or aggregated primary particles. When these are pressed, bonds are established between the particles or granules, thereby conferring a certain mechanical strength to the pressed tablet.

It should be noted that the above-introduced terms: powder, primary particles and aggregated primary particles may be somewhat misleading in the sense that the difference between primary particles and aggregated primary particles may very often be looked upon differently depending on the background of the user. Some may for instance regard a sweetener, such as sorbitol, as a primary particle in spite of the fact that sorbitol due to the typically preprocessing performed on sorbitol when delivered to the customer should rather be regarded as some sort of aggregated primary particles. The definition adopted in the description of this invention is that aggregated primary particles refer to macro-particles comprising more or less preprocessed primary particles.

When pressure is applied to the particles, the bulk volume is reduced, and the amount of air is decreased. During this process energy is consumed. As the particles come into closer proximity to each other during the volume reduction process, bonds may be established between the particles or granules. The formation of bonds is associated with a reduction in the energy of the system as energy is released. Volume reduction takes place by various mechanisms and different types of bonds may be established between the particles or granules depending on the pressure applied and the properties of the particles or granules. The first thing that happens when a powder is pressed is that the particles are rearranged under low compaction pressures to form a closer packing structure. Particles with a regular shape appear to undergo rearrangement more easily than those of irregular shape. As the pressure increases, further rearrangement is prevented, and subsequent volume reduction is obtained by plastic and elastic deformation and/or fragmentation of the tablet particles. Brittle particles are likely to undergo fragmentation, i.e. breakage of the original particles into smaller units. Plastic deformation is an irreversible process resulting in a permanent change of particle shape, whereas the particles resume their original shape after elastic deformation. Evidently, both plastic and elastic deformation may occur, when compressing a chewing gum tablet.

Several studies of the bond types in pressed tablets have been made over the years, typically in the context of pharmaceuticals and several techniques of obtaining pressed tablets on the basis of available powders has been provided. Such studies have been quite focused on what happens when the volume reduction is performed and how the end-product may be optimized for the given purpose. Several refinements with respect to pressed tablets has for instance been made in the addition of for example binders in the tablet raw materials for the purpose of obtaining a sufficient strength to the final pressed tablet while maintaining acceptable properties, e.g. with respect to release.

Contrary to the tableted chewing gum composition according to the invention, conventional chewing gum (which is mentioned here for reference purposes) may be manufactured by sequentially adding the various chewing gum ingredients to a commercially available mixer known in the art where the finished gum base is already present. After the initial ingredients have been thoroughly mixed, the gum mass is discharged from the mixer and shaped into the desired form such as by rolling into sheets and cutting into sticks, extruded into chunks or casting into pellets. Generally, the ingredients of conventional chewing gum may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor have been added. The entire mixing procedure typically takes from thirty to forty minutes, but longer mixing times may sometimes be required. Those skilled in the art will recognize that many variations of the above described procedure may be followed.

In accordance with the invention, the tableted chewing gum according to the invention may comprise about 0.1 to about 75% by weight of an outer coating applied onto the chewing gum centre. Thus, suitable coating types include hard coatings, film coatings and soft coatings of any composition including those currently used in coating of tableted chewing gum.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer and it may moreover protect the gum centres for various reasons. In a typical process of providing the chewing gum centres with a protective sugar coating, the gum centres are successively treated in suitable coating equipment with aqueous solutions of crystallisable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or active compounds.

In a typical hard coating process as it will be described in detail in the following, a suspension containing crystallisable sugar and/or polyol is applied onto the gum centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished chewing gum element, such as about 10 to about 60% by weight, including about 15 to about 50% by weight.

In further useful embodiments, the outer coating of the chewing gum element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a chewing gum centre of any of the above forms. The thickness of such a coating is usually between 20 and 100 m.

Generally, the film coating is obtained by passing the chewing gum centres through a spray zone with atomized droplets of the coating materials in a suitable aqueous or organic solvent vehicle, after which the material adhering to the gum centres is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of the chewing gum formulation. Such release modifying polymers include methylacrylate ester copolymers, ethylcellulose (EC) and enteric polymers designed to resist the acidic stomach environment. The latter group of polymers include: cellulose acetate phtalate (CAP), polyvinyl acetate phtalate (PVAP), shellac, metacrylic acid copolymers, cellulose acetate trimellitate (CAT) and HPMC. It will be appreciated that the outer film coating according to the present invention may comprise any combination of the above film-coating polymers.

According to the invention, the one or more cannabinoids may be selected from various cannabinoids.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which may have high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that the additional components such as secondary and minor cannabinoids and the non-cannabinoid fraction have been substantially removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

In the context of this application the terms "cannabinoid extract" or "extract of cannabinoids", which are used interchangeably, encompass "Botanical Drug Substances" derived from cannabis plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of cannabis, "botanical drug substances" derived from cannabis plants do not include highly purified, Pharmacopoeial grade cannabinoids.

The term "Cannabis plant(s)" encompasses wild type *Cannabis sativa* and also variants thereof, including cannabis chemovars which naturally contain different amounts of the individual cannabinoids, *Cannabis sativa* subspecies indica including the variants var. indica and var. *kafiristanica, Cannabis indica, Cannabis ruderalis* and also plants which are the result of genetic crosses, self-crosses or hybrids thereof. The term "Cannabis plant material" is to be interpreted accordingly as encompassing plant material derived from one or more cannabis plants. For the avoidance of doubt it is hereby stated that "cannabis plant material" includes dried cannabis biomass.

Preferably the one or more cannabinoids are selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC. This list is not exhaustive and merely details the cannabinoids which are identified in the present application for reference.

So far, more than 120 different phytocannabinoids have been identified which are within the scope of the present invention.

Cannabinoids can be split into different groups as follows: Phytocannabinoids; Endocannabinoids; and Synthetic cannabinoids.

Cannabinoid receptors can be activated by three major groups of agonist ligands, for the purposes of the present invention and whether or not explicitly denominated as such herein, lipophilic in nature and classed respectively as: endocannabinoids (produced endogenously by mammalian cells); phytocannabinoids (such as cannabidiol, produced by the cannabis plant); and, synthetic cannabinoids (such as HU-210).

Phytocannabinoids can be found as either the neutral carboxylic acid form or the decarboxylated form depending on the method used to extract the cannabinoids. For example, it is known that heating the carboxylic acid form will cause most of the carboxylic acid form to decarboxylate.

Phytocannabinoids can also occur as either the pentyl (5 carbon atoms) or propyl (3 carbon atoms) variant. For example, the phytocannabinoid THC is known to be a CB1 receptor agonist whereas the propyl variant THCV has been discovered to be a CB1 receptor antagonist meaning that it has almost opposite effects.

According to the invention, examples of phytocannabinoids may be cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC.

The formulation according to the present invention may also comprise at least one cannabinoid selected from those disclosed in A. Douglas Kinghorn et al., Phytocannabinoids, Vol. 103, Chapter 1, pages 1-30.

Examples of endocannabinoids are molecules that activate the cannabinoid receptors within the body. Examples include 2-arachidonyl glycerol (2AG), 2-arachidonyl glyceryl ether (2AGE), arachidonyl dopamine, and arachidonyl ethanolamide (anandamide). Structurally related endogenous molecules have been identified that share similar structural features, but that display weak or no activity towards the cannabinoid receptors but are also termed endocannabinoids.

Examples of these endocannabinoid lipids include 2-acyl glycerols, alkyl or alkenyl glyceryl ethers, acyl dopamines and N-acylethanolamides that contain alternative fatty acid or alcohol moieties, as well as other fatty acid amides containing different head groups. These include N-acylserines as well as many other N-acylated amino acids. Examples of cannabinoid receptor agonists are neuromodulatory and affect short-term memory, appetite, stress response, anxiety, immune function and analgesia.

In one embodiment the cannabinoid is palmitoylethanolamide (PEA) which is an endogenous fatty acid amide belonging to the class of nuclear factor agonists.

Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

It is preferred that the formulation comprises one or two primary cannabinoids, which are preferably selected from the group consisting of, cannabidiol (CBD) or cannabidivarin (CBDV), tetrahydrocannabinol (THC), tetrahydrocannabivarin (THCV), tetrahydrocannabinolic acid (THCA), cannabigerol (CBG) and cannabidiolic acid (CBDA) or a combination thereof. It is preferred that the formulation comprises cannabidiol and/or tetrahydrocannabinol.

Preferably, the chewing gum of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In a further aspect of the present invention the oral cannabinoid formulation is suitable for use in the treatment of conditions requiring the administration of a neuroprotectant or anti-convulsive medication.

The oral cannabinoid formulation may be for use in the treatment of seizures.

The oral cannabinoid formulation may be for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, cannabis use disorder, post-traumatic stress disorder, anxiety, early psychosis, Alzheimer's disease, and autism.

The following non-limiting examples illustrate different variations of the present invention. The examples are meant for indicating the inventive concept; hence the mentioned examples should not be understood as exhaustive for the present. In particular, CBD is used as an exemplary compound, but may also be another cannabinoid.

EXAMPLES

Example 1

A: Preparation of Water Insoluble Gum Base Particles

Twenty different water-insoluble gum base compositions were prepared. The gum base compositions were prepared in the process as described below. In subsequent examples, the specific compositions of the gum bases (GB10 to GB29) are outlined.

In all of the gum base examples, the amount of the various ingredients is given as % by weight of the gum base.

Elastomers and elastomer plasticizer (PVA) were mixed at 120° C. together with filler, either calcium carbonate or talc, in a mixer having horizontally placed Z-shaped arms for mixing. It is noted that PVA was applied as an elastomer plasticizer for the elastomers in the composition and not in form of an elastomer. PVA as an elastomer plasticizer has special properties in the present context. For some of the comparative examples, another comparative polymer was added together with the elastomers and elastomer plasticizer and mixed together with the elastomer and the elastomer plasticizer. Natural resins were added after about 30 minutes of mixing of the polymers. Once the polymers and the natural resins had softened in the composition, additional ingredients were added, such as triacetin, emulsifier, wax, antioxidants, calcium carbonate, talc, titan dioxide and vegetable fat. A part of the calcium carbonate or talc may be substituted by titan dioxide.

After a total mixing time of about 90-105 minutes, the mixture was discharged into a pan and allowed to cool at room temperature. For some of the examples where butyl rubber (BR) was added as an elastomer, the mixing time was optionally extended to a total of about 110-115 minutes depending on the amount of optional fillers.

The gum compositions were further processed in an extruder (Leistrits ZSE/BL 360 kw 104, available from GALA GmbH, Germany). The gum compositions were extruded through a die plate into a liquid filled chamber (granulator A5 PAC 6, available from GALA GmbH, Germany).

The extruder delivered the composition at a feed rate of 250 kg/h to the die plate. The extruder screw speed was 247 rpm. The temperature in the extruder was about 80° C. and was mainly regulated by the temperature of the gum compositions that were only allowed to cool slightly prior to being introduced into the extruder. The extruder produced a pressure difference of 71 bar.

The gum composition was extruded through the die plate, which was heated to a temperature of 177° C. and had 336 holes with diameter 0.36 mm. In the granulator chamber the extruded composition was cut to particles by a cutter with 8 blades and cutter speed about 2000 rpm. The particles were cooled and transported to a strainer unit (a centrifugal dryer TWS 20, available from GALA GmbH, Germany) in water with temperature about 10° C. and flow 22 m³/h. The average cooling and transport time in water was approx. 2 seconds. The granule rate was 250 kg/h and the average diameter of the obtained particles was 1.24 mm. The particles correspond to a first population of particles comprising water-insoluble gum base. These particles were used for tableting.

Example 2

Various Gum Base Formulations

TABLE 1A

| GB number | GB10 | GB11 | GB12 | GB13 | GB14 |
|---|---|---|---|---|---|
| PVA | 25 | 18 | 30 | 10 | 40 |
| PIB | 5 | 10 | 5 | 10 | 5 |
| BR | 5 | 5 | 5 | 5 | — |
| Nat. resin | 25 | 20 | 20 | 35 | 15 |
| Calcium Carbonate | 17 | — | 17 | 17 | 17 |
| Talc | — | 17 | — | — | — |
| Triacetin | — | 7 | — | — | — |
| Emulsifier | 5 | 10 | 5 | 5 | 5 |
| Wax | 13 | 13 | 13 | 13 | 13 |
| Veg. fat | 5 | — | 5 | 5 | 5 |
| Total | 100 | 100 | 100 | 100 | 100 |

Gum base compositions,
PVA = polyvinyl acetate (Vinnapas B 1.5 sp., supplied by Wacker);
PIB = polyisobutylene (Oppanol B12, supplied by BASF);
BR = butyl rubber (isobutylene-isoprene copolymer);
Nat. resin = glycerol ester of hydrogenated gum rosin;
Veg. fat = vegetable fat.

Example 3

Various Gum Base Formulations

TABLE 1B

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat.

| GB number | GB15 | GB16 | GB17 | GB18 | GB19 |
|---|---|---|---|---|---|
| PVA | 25 | 25 | 20 | 40 | 15 |
| PI13 | 5 | 10 | 5 | 5 | 5 |
| BR | 5 | 5 | 5 | 5 | — |
| Nat. resin | 25 | 20 | 30 | 10 | 40 |
| Calcium Carbonate | 17 | 17 | 17 | 17 | 17 |
| Talc | — | — | — | — | — |
| Triacetin | — | — | — | — | — |
| Emulsifier | 5 | 5 | 5 | 5 | 5 |
| Wax | 13 | 13 | 13 | 13 | 13 |
| Veg. fat | 5 | 5 | 5 | 5 | 5 |
| Total | 100 | 100 | 100 | 100 | 100 |

Example 4

Various Gum Base Formulations

TABLE 1C

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; Veg. fat = vegetable fat; Acesulfame K (HIS = high-intensity sweetener); Menthol (flavor); BHT (Butylated hydroxytoluene = antioxidant).

| GB number | GB20 | GB21 | GB22 | GB23 | GB24 |
|---|---|---|---|---|---|
| PVA | 18 | 18 | 18 | 18 | 18 |
| PIB | 10 | 10 | 10 | 10 | 10 |
| BR | 5 | 5 | 5 | 5 | 5 |
| Nat. resin | 20 | 20 | 20 | 20 | 20 |
| Calcium Carbonate | — | — | — | — | — |
| Talc | 14 | 16.5 | 13.5 | 17 | 14 |
| Triacetin | 7 | 7 | 7 | 7 | 7 |
| Emulsifier | 10 | 10 | 10 | 10 | 10 |
| Wax | 13 | 13 | 13 | 13 | 13 |
| Veg. fat | — | — | — | — | — |
| Acesulfame K | — | 0.5 | 0.5 | — | — |
| Menthol | 3 | — | 3 | — | 3 |
| BHT | — | — | — | 0.04 | 0.04 |
| Total | 100 | 100 | 100 | 100 | 100 |

Example 5

Various Gum Base Formulations

TABLE 1D

Gum base compositions, PVA = polyvinyl acetate (Vinnapas B 1.5 sp., supplied by Wacker); PIB = polyisobutylene (Oppanol B12, supplied by BASF); BR = butyl rubber (isobutylene-isoprene copolymer); Nat. resin = glycerol ester of hydrogenated gum rosin; VA-VL = vinyl acetate-vinyl laurate copolymer (Vinnapas B 500/40VL, supplied by Wacker); Veg. fat = vegetable fat.

| GB number | GB25 | GB26 | GB27 | GB28 | GB29 |
|---|---|---|---|---|---|
| PVA | 25 | 18 | 30 | 30 | 20 |
| PI13 | 5 | 10 | 5 | 3 | 3 |
| BR | 5 | 5 | — | 2 | 2 |
| Nat. resin | 25 | 20 | — | — | 20 |
| VA-VL | — | — | 20 | 20 | 10 |
| Calcium Carbonate | 17 | — | 17 | 17 | 17 |
| Talc | — | 17 | — | — | — |
| Triacetin | — | 7 | — | — | 2 |
| Emulsifier | 5 | 10 | 11 | 11 | 9 |
| Wax | 13 | 13 | 12 | 12 | 12 |
| Veg. fat | 5 | — | 5 | 5 | 5 |
| Total | 100 | 100 | 100 | 100 | 100 |

Example 6

CBD Extract 52%

CBD extract with a 52% content of CBD provided by CBDepot (batch number CSFF 2018/5) was preheated to around 60° C. for around 0.5 to 1 hour until the extract was in liquid form. The extract had a content of fatty acids, glycerol, waxes, terpenes and flavonoids. After the preheating process, the extract was applied as a thin layer on top of one or more sugar alcohol particles, here isomalt. After mixing until CBD was homogeneously distributed in the isomalt, the mixture was sieved through a 1400 microns sieve.

Example 7

CBD Extract 10%

CBD extract with a 10% content of CBD provided by Medical Hemp (batch number MH131B Gold), was preheated to around 60° C. for around 0.5 to 1 hour until the extract was in liquid form. The extract had a content of fatty acids, glycerol, waxes, terpenes and flavonoids. After the preheating process, the extract was applied as a thin layer on top of one or more sugar alcohol particles, here isomalt. After mixing until CBD was homogeneously distributed in the isomalt, the mixture was sieved through a 1400 microns sieve.

Example 8

CBD Isolate

CBD isolate from cannabis plant tissues (phytocannabinoid) with a 98.5% content of CBD provided by Medical Hemp (batch number MH18212) was dissolved in an 96% ethanol solution. The ratio between the CBD isolate and ethanol was 1:1. Once CBD was dissolved in the ethanol, the CBD isolate was applied in a premix with one or more sugar alcohol particles, here isomalt. After mixing until CBD was homogeneously distributed in the isomalt, the mixture was sieved through a 1400 microns sieve.

Example 9

Preparation of Cannabinoid Sugar Alcohol Premix

A premix was made with CBD and sugar alcohol particles, here isomalt. The premix was made in a weight ratio of about 1:20 of CBD and isomalt with either one of the forms of CBD outlined in Examples 6-8. CBD was added to the sugar alcohol particles and the powder was blended.

Example 10

Preparation of Cannabinoid Cyclodextrin Premix

CBD (extract or isolate) was added and dissolved in a 5% solution of polysorbate 80 to obtain a 10% solution of CBD. The 10% CBD solution was slowly added and mixed into a solution with 10% cyclodextrin to form a CBD-cyclodextrin complex. The water was removed, whereupon the complex was applied in a premix with water-soluble chewing gum ingredients, here isomalt. After mixing until CBD was homogeneously distributed in the isomalt, the mixture was sieved through a 1400 microns sieve.

Example 11

Preparation of Cannabinoid Microcrystalline Cellulose Premix

A cannabinoid-microcrystalline cellulose (MCC) premix was made by first adding free cannabinoid to poloxamer F68 (PF) to obtain a 10% blend of cannabinoid in poloxamer F68. Butylated hydroxytoluene (BHT) was added (0.5%) to 50 grams of the cannabinoid-poloxamer F68 solid mix and added to 50 grams of microcrystalline cellulose provided as Avicel PH 102 from FMC Biopolymer. This was then mixed in a Kitchenaid mixer operated at about 30 RPM for about 30 minutes at room temperature. This mixture was equilibrated for about 30 minutes in a sealed container. Hereby, at 5% cannabinoid-MCC premix was obtained.

Example 12

A: Preparation of Tableted Chewing Gum with One Gum Layer

A first population of particles comprising water-insoluble gum base prepared according to Example 1 and formulated according to Examples 2-5 (GB) was mixed with a second population of particles comprising water-soluble chewing gum ingredients. Optionally, further population of particles were added as well as further optional ingredients.

The mixture was blended in a mixing container at 7-12 rpm and optionally loaded with processing aid in order to improve free-flowing properties of the particles. The mixture was subsequently led to a standard tablet pressing machine (3090i, available from Fette GmbH) comprising dosing apparatus (P 3200 C, available from Fette GmbH, Germany) and pressed into tableted chewing gum compositions. The filling depth in the apparatus was 7.5 mm and the diameter 15.0 mm. The tablets were pressed using a pressing pressure of 33.0-33.6 kN and optionally prepressed with a pressing pressure of 1-7 kN. There were 75 punches on the rotor, and the rotor speed used was 11 rpm. The individual tablets had a weight of approx. 1.35 g.

B: Preparation of Tableted Chewing Gum with One Gum Layer

A first population of particles comprising water-insoluble gum base in an amount of 36% by weight of particles was prepared according to Example 1 and formulated according to Examples 2-5 (GB). In this Example, about 56% of isomalt was included in the first population of particles (unless stated otherwise), i.e. gum base and isomalt was included in the same individual particles. Optionally, further population of particles were added as well as further optional ingredients.

The mixture was blended in a mixing container at 7-12 rpm and optionally loaded with processing aid in order to improve free-flowing properties of the particles. The mixture was subsequently led to a standard tablet pressing machine (3090i, available from Fette GmbH) comprising dosing apparatus (P 3200 C, available from Fette GmbH, Germany) and pressed into tableted chewing gum compositions. The filling depth in the apparatus was 7.5 mm and the diameter 15.0 mm. The tablets were pressed using a pressing pressure of 33.0-33.6 kN and optionally prepressed with a pressing pressure of 1-7 kN. There were 75 punches on the rotor, and the rotor speed used was 11 rpm. The individual tablets had a weight of approx. 1.35 g.

Example 13

A: Preparation of Tableted Chewing Gum with One Layer Free of Gum Base

A population of particles comprising water-soluble chewing gum ingredients was provided. Optionally, further population of particles were added as well as further optional ingredients. However, gum base particles were not applied.

Before pressing, the mixture was blended in a mixing container at 7-12 rpm and optionally loaded with processing aid in order to improve free-flowing properties of the particles. The mixture was subsequently led to a standard tablet pressing machine (3090i, available from Fette GmbH) comprising dosing apparatus (P 3200 C, available from Fette GmbH, Germany) and pressed into a layer of the tableted chewing gum compositions. The filling depth in the apparatus was 7.5 mm and the diameter 15.0 mm. The layer of the tablet was pressed using a pressing pressure of 33.0-33.6 kN. There were 75 punches on the rotor, and the rotor speed used was 11 rpm.

Subsequently, a layer according to Example 12A was tableted on top of the prepared layer (does not apply for B-F below). The weight ratio of the two layers was 55 to 45 (gum base free layer to gum base layer). The individual tablets had a weight of approx. 1.6 g.

B: Preparation of Tableted Chewing Gum with One Layer Free of Gum Base

One layer was prepared according to Example 13A. Subsequently, another layer according to Example 12B was tableted on top of the prepared layer. The weight ratio of the two layers was 50 to 50 (Gum base free layer to gum base layer). The individual tablets had a weight of approx. 1.6 g.

C: Preparation of Tableted Chewing Gum with Two Gum Base Layers

One layer was prepared according to Example 12A. Subsequently, another layer according to Example 12A was tableted on top of the prepared layer. The weight ratio of the two layers was 50 to 50 (Gum base layer to gum base layer). The individual tablets had a weight of approx. 1.6 g.

D: Preparation of Tableted Chewing Gum with Three Layers

One layer was prepared according to Example 13A. Subsequently, another layer according to Example 12A was tableted on top of the prepared layer. Subsequently, a further layer according to Example 13A was tableted on top of the layer from Example 12A. The weight ratio of the three layers was 35 to 30 to 35 (gum base free layer to gum base layer to gum base free layer). The individual tablets had a weight of approx. 1.6 g.

E: Preparation of Tableted Chewing Gum with Two Layers and a Gel Capsule Module

One layer was prepared according to Example 13A. Subsequently, a module of non-particulate material was located centrally on top of the prepared layer. In this example the non-particulate material was a gel capsule. Subsequently, another layer according to Example 12A was tableted on top of and fully enclosing the non-particulate material. The weight ratio was 45 to 10 to 45 (gum base free layer to non-particulate material to gum base layer). The individual tablets had a weight of approx. 1.6 g.

F: Preparation of Tableted Chewing Gum with Two Layers and Gum Module

One layer was prepared according to Example 13A. Subsequently, a module of non-particulate material was located on top of the prepared layer. In this example the non-particulate material was a sheet of conventional extruded chewing gum. Subsequently, another layer according to Example 12A was tableted on top of the sheet of extruded gum, the sheet being visible as a layer from a side view of the tablet. The weight ratio was 45 to 10 to 45 (Gum base free layer to non-particulate material to gum base layer). The individual tablets had a weight of approx. 1.6 g.

Example 14

Composition of Tableted Cannabinoid Chewing Gum

Cannabinoid chewing gum based on the procedure in Example 12A was made with the formulations outlined in the examples below. The tableted chewing gum had a weight of about 1.35 g for each piece and a content of CBD of 10 mg for each piece. In all of the chewing gum examples, the amount of the various ingredients is given as % by weight of the chewing gum.

TABLE 1E

It was secured that CBD was thoroughly mixed into the premixture as outlined in Example 9.
CBD 52%* was prepared according to Example 6.

| | CG Number | | | | |
|---|---|---|---|---|---|
| | CG100 | CG101 | CG102 | CG103 | CG104 |
| GB10 | 36 | — | — | — | — |
| GB11 | — | 36 | — | — | — |
| GB12 | — | — | 36 | — | — |
| GB13 | — | — | — | 36 | — |
| GB14 | — | — | — | — | 36 |
| Isomalt | 56.4 | 56.4 | 56.4 | 56.4 | 56.4 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 2.1 | 2.1 | 2.1 | 2.1 | 2.1 |
| CBD 52%* | 1.4 | 1.4 | 1.4 | 1.4 | 1.4 |
| Total | 100 | 100 | 100 | 100 | 100 |

Example 15

Composition of Tableted Cannabinoid Chewing Gum

Cannabinoid chewing gum based on the procedure in Example 12A was made with the formulations outlined in the examples below. The tableted chewing gum had a weight of about 1.35 g for each piece and a content of CBD of 10 mg for each piece. In all of the chewing gum examples, the amount of the various ingredients is given as % by weight of the chewing gum.

TABLE 1F

It was secured that CBD was thoroughly mixed into the premixture as outlined in Example 9.
CBD 52%* was prepared according to Example 6.

| | CG Number | | | | |
|---|---|---|---|---|---|
| | CG105 | CG106 | CG107 | CG108 | CG109 |
| GB15 | 36 | — | — | — | — |
| GB16 | — | 36 | — | — | — |
| GB17 | — | — | 36 | — | — |
| GB18 | — | — | — | 36 | — |
| GB19 | — | — | — | — | 36 |

TABLE 1F-continued

It was secured that CBD was thoroughly mixed into the premixture as outlined in Example 9.
CBD 52%* was prepared according to Example 6.

|  | CG Number | | | | |
| --- | --- | --- | --- | --- | --- |
|  | CG105 | CG106 | CG107 | CG108 | CG109 |
| Isomalt | 56.4 | 56.4 | 56.4 | 56.4 | 56.4 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 2.1 | 2.1 | 2.1 | 2.1 | 2.1 |
| CBD 52%* | 1.4 | 1.4 | 1.4 | 1.4 | 1.4 |
| Total | 100 | 100 | 100 | 100 | 100 |

Example 16

Composition of Tableted Cannabinoid Chewing Gum

Cannabinoid chewing gum based on the procedure in Example 12A was made with the formulations outlined in the examples below. The tableted chewing gum had a weight of about 1.35 g for each piece and a content of CBD of 10 mg for each piece. In all of the chewing gum examples, the amount of the various ingredients is given as % by weight of the chewing gum.

TABLE 1G

It was secured that CBD was thoroughly mixed into the premixture as outlined in Example 9.
CBD 52%* was prepared according to Example 6.

|  | CG Number | | | | |
| --- | --- | --- | --- | --- | --- |
|  | CG110 | CG111 | CG112 | CG113 | CG114 |
| GB20 | 36 | — | — | — | — |
| GB21 | — | 36 | — | — | — |
| GB22 | — | — | 36 | — | — |
| GB23 | — | — | — | 36 | — |
| GB24 | — | — | — | — | 36 |
| Isomalt | 56.4 | 56.4 | 56.4 | 56.4 | 56.4 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 2.1 | 2.1 | 2.1 | 2.1 | 2.1 |
| CBD 52%* | 1.4 | 1.4 | 1.4 | 1.4 | 1.4 |
| Total | 100 | 100 | 100 | 100 | 100 |

Example 17

Composition of Tableted Cannabinoid Chewing Gum

Cannabinoid chewing gum based on the procedure in Example 12A was made with the formulations outlined in the examples below. The tableted chewing gum had a weight of about 1.35 g for each piece and a content of CBD of 10 mg for each piece. In all of the chewing gum examples, the amount of the various ingredients is given as % by weight of the chewing gum.

TABLE 1H

It was secured that CBD was thoroughly mixed into the premixture as outlined in Example 9.
CBD 52%* was prepared according to Example 6.

|  | CG Number | | | | |
| --- | --- | --- | --- | --- | --- |
|  | CG115 | CG116 | CG117 | CG118 | CG119 |
| GB25 | 36 | — | — | — | — |
| GB26 | — | 36 | — | — | — |
| GB27 | — | — | 36 | — | — |
| GB28 | — | — | — | 36 | — |
| GB29 | — | — | — | — | 36 |
| Isomalt | 56.4 | 56.4 | 56.4 | 56.4 | 56.4 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 2.1 | 2.1 | 2.1 | 2.1 | 2.1 |
| CBD 52%* | 1.4 | 1.4 | 1.4 | 1.4 | 1.4 |
| Total | 100 | 100 | 100 | 100 | 100 |

Example 18

Composition of Tableted Cannabinoid Chewing Gum

Cannabinoid chewing gum based on the procedure in Example 12A (CG120-121) and 12B (CG122-123) was made with the formulations outlined in the examples below. One reference example was made with extruded chewing gum made by rolling and scoring according to conventional principles (CG124). The chewing gum had a weight of about 1.35 g for each piece and a content of CBD of 10 mg for each piece. In all of the chewing gum examples, the amount of the various ingredients is given as % by weight of the chewing gum.

TABLE 1I

It was secured that CBD was thoroughly mixed into the premixture as outlined in Example 9. CBD 52%* was prepared according to Example 6. CG124 is a reference example made by rolling and scoring (conventional extruded chewing gum).

|  | CG Number | | | | |
| --- | --- | --- | --- | --- | --- |
|  | CG120 | CG121 | CG122 | CG123 | CG124* |
| GB10 | 36 | 36 | 36 | 36 | 36 |
| Isomalt | 40.6 | 56.4 | 40.6 | 56.4 | 56.4 |
| Talc | 15.8 | — | 15.8 | — | — |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 2.1 | 2.1 | 2.1 | 2.1 | 2.1 |
| CBD 52%* | 1.4 | 1.4 | 1.4 | 1.4 | 1.4 |
| Total | 100 | 100 | 100 | 100 | 100 |

Example 19

Composition of Tableted Cannabinoid Chewing Gum

Cannabinoid chewing gum based on the procedure in Example 12A was made with the formulations outlined in the examples below. The tableted chewing gum had a weight of about 1.35 g for each piece and a content of CBD of 10 mg for each piece. In all of the chewing gum examples, the amount of the various ingredients is given as % by weight of the chewing gum.

TABLE 1J

It was secured that CBD was thoroughly mixed into
the premixture as outlined in Example 9.
CBD 52%* was prepared according to Example 6.

| | CG Number | | | | |
|---|---|---|---|---|---|
| | CG125 | CG126 | CG127 | CG128 | CG129 |
| GB10 | 62.4 | 52.4 | 42.4 | 32.4 | 22.4 |
| Isomalt | 30 | 40 | 50 | 60 | 70 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 2.1 | 2.1 | 2.1 | 2.1 | 2.1 |
| CBD 52%* | 1.4 | 1.4 | 1.4 | 1.4 | 1.4 |
| Total | 100 | 100 | 100 | 100 | 100 |

Example 20

Composition of Tableted Cannabinoid Chewing Gum

Cannabinoid chewing gum based on the procedure in Example 13A (CG130-133) and 13B (CG134) were made with the formulations outlined in the examples below. The tableted chewing gum had a weight of about 1.6 g for each piece and a content of CBD of 10 mg for each piece. The weight ratio of the two layers was 55 to 45 (gum base free layer to gum base layer) for CG130-133 and 50 to 50 for CG134. In all of the chewing gum examples, the amount of the various ingredients is given as % by weight of the layer of the tableted chewing gum.

TABLE 1K

It was secured that CBD was thoroughly mixed into the
premixture as outlined in Example 9.
CBD 52%* was prepared according to Example 6.

| | CG Number | | | | |
|---|---|---|---|---|---|
| | CG130 | CG131 | CG132 | CG133 | CG134 |
| Layer 1 | | | | | |
| GB10 | 36 | 60 | 60 | 80 | 36 |
| Isomalt | 58.9 | 34.9 | 32.2 | 14.9 | 58.9 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 1 | 1 | 1 | 1 | 1 |
| CBD 52%* | — | — | 2.7 | — | — |
| Total | 100 | 100 | 100 | 100 | 100 |

TABLE 1L

It was secured that CBD was thoroughly mixed into
the premixture as outlined in Example 9.
CBD 52%* was prepared according to Example 6.

| | CG Number | | | | |
|---|---|---|---|---|---|
| | CG130 | CG131 | CG132 | CG133 | CG134 |
| Layer 2 | | | | | |
| GB10 | — | — | — | — | — |
| Isomalt | 94.2 | 94.2 | 96.4 | 94.2 | 94.0 |
| Menthol powder | 2.5 | 2.5 | 2.5 | 2.5 | 2.5 |
| Eucalyptus Powder | — | — | — | — | — |

TABLE 1L-continued

It was secured that CBD was thoroughly mixed into
the premixture as outlined in Example 9.
CBD 52%* was prepared according to Example 6.

| | CG Number | | | | |
|---|---|---|---|---|---|
| | CG130 | CG131 | CG132 | CG133 | CG134 |
| Acesulfame K | 0.05 | 0.05 | 0.05 | 0.05 | 0.05 |
| Sucralose | 0.05 | 0.05 | 0.05 | 0.05 | 0.05 |
| Processing aid | 1 | 1 | 1 | 1 | 1 |
| CBD 52%* | 2.2 | 2.2 | — | 2.2 | 2.4 |
| Total | 100 | 100 | 100 | 100 | 100 |

Example 21

Composition of Tableted Cannabinoid Chewing Gum

Cannabinoid chewing gum based on the procedure in Example 13C (CG135-137) and 13D (CG138-139) were made with the formulations outlined in the examples below. The tableted chewing gum had a weight of about 1.6 g for each piece and a content of CBD of 10 mg for each piece. The weight ratio of the two layers was 50 to 50 for CG135-137 and 35 to 30 to 35 for CG138-139. In all of the chewing gum examples, the amount of the various ingredients is given as % by weight of the layer of the tableted chewing gum.

TABLE 1M

It was secured that CBD was thoroughly mixed
into the premixture as outlined in Example 9.
CBD 52%* was prepared according to Example 6.

| | CG Number | | | | |
|---|---|---|---|---|---|
| | CG135 | CG136 | CG137 | CG138 | CG139 |
| Layer 1 | | | | | |
| GB10 | 36 | 60 | 60 | 36 | 60 |
| Isomalt | 58.9 | 34.9 | 32.5 | 58.9 | 34.9 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Processing aid | 1 | 1 | 1 | 1 | 1 |
| CBD 52%* | — | — | 2.4 | — | — |
| Total | 100 | 100 | 100 | 100 | 100 |

TABLE 1N

It was secured that CBD was thoroughly mixed into the premixture as outlined in Example 9. CBD 52%* was prepared according to Example 6. It is noted that CG 138* and CG 139* were made with 3 layers, where layer 1 was the middle layer and layer 2 and 3 were located on opposite sides of layer 1. CG 135-137 were made with two gum layers.

| | CG Number | | | | |
|---|---|---|---|---|---|
| | CG135 | CG136 | CG137 | CG138* | CG139* |
| Layer 2 (and 3*) | | | | | |
| GB10 | 36 | 36 | 36 | — | — |
| Isomalt | 56.5 | 56.5 | 58.9 | 94.7 | 94.7 |
| Menthol powder | 2 | 2 | 2 | 2.5 | 2.5 |
| Eucalyptus Powder | 2 | 2 | 2 | — | — |
| Acesulfame K | 0.05 | 0.05 | 0.05 | 0.05 | 0.05 |

TABLE 1N-continued

It was secured that CBD was thoroughly mixed into the premixture as outlined in Example 9. CBD 52%* was prepared according to Example 6. It is noted that CG 138* and CG 139* were made with 3 layers, where layer 1 was the middle layer and layer 2 and 3 were located on opposite sides of layer 1. CG 135-137 were made with two gum layers.

| | CG Number | | | | |
|---|---|---|---|---|---|
| | CG135 | CG136 | CG137 | CG138* | CG139* |
| Sucralose | 0.05 | 0.05 | 0.05 | 0.05 | 0.05 |
| Processing aid | 1 | 1 | 1 | 1 | 1 |
| CBD 52%* | 2.4 | 2.4 | — | 1.7 | 1.7 |
| Total | 100 | 100 | 100 | 100 | 100 |

Example 22

Composition of Tableted Cannabinoid Chewing Gum

Cannabinoid chewing gum based on the procedure in Example 12A was made with the formulations outlined in the examples below. The tableted chewing gum had a weight of about 1.35 g for each piece and a content of CBD of 10 mg for each piece. In all of the chewing gum examples, the amount of the various ingredients is given as % by weight of the chewing gum.

TABLE 1O

It was secured that CBD was thoroughly mixed into the premixture as outlined in Example 9.
CBD 52%* was prepared according to Example 6.
CBD-MCC 5%* was prepared according to Example 11.
CBD-MCC 10%* was prepared according to Example 11 with a higher amount of CBD.
CBD-cyclodex* is CBD-cyclodextrin complex prepared according to Example 10 and 25% loaded. Self-emulsifting* was prepared with a self-emulsifier, here polysorbate.

| | CG Number | | | | |
|---|---|---|---|---|---|
| | CG140 | CG141 | CG142 | CG143 | CG144 |
| GB10 | 36 | 36 | 36 | 36 | 36 |
| Isomalt | 56.4 | 43.0 | 50.4 | 54.8 | 55.4 |
| Menthol powder | 2 | 2 | 2 | 2 | 2 |
| Eucalyptus Powder | 2 | 2 | 2 | 2 | 2 |
| Acesulfame K | 0.05 | 0.05 | 0.05 | 0.05 | 0.05 |
| Sucralose | 0.05 | 0.05 | 0.05 | 0.05 | 0.05 |
| Anti-sticking agent | 2.1 | 2.1 | 2.1 | 2.1 | 2.1 |
| CBD 52%* | 1.4 | — | — | — | 1.4 |
| CBD-MCC 5%* | — | 14.8 | — | — | — |
| CBD-MCC 10%* | — | — | 7.4 | — | — |
| CBD-cyclodex* | — | — | — | 3.0 | — |
| Self-emulsifying* | — | — | — | — | 1 |
| Total | 100 | 100 | 100 | 100 | 100 |

Example 23

Coating of Tableted Chewing Gum

A hard coating was prepared for selected samples with the following composition:

TABLE 1P

It was secured that CBD was thoroughly mixed into the premixture as outlined in Example 9.
CBD 52%* was prepared according to Example 6.
CBD isolate* was prepared according to Example 8.
The coating was provided to samples of CG 100 from Example 15.
Hard coating

| | % by weight Number | |
|---|---|---|
| Ingredients | CG145 | CG146 |
| Maltitol | 56.9 | 56.9 |
| Water | 22.7 | 24.8 |
| Mannitol | 11 | 11 |
| gummi arabicum | 4 | 4 |
| Titandioxid | 1 | 1 |
| Polysorbate | 0.1 | 0.1 |
| CBD 52%* | 4.3 | — |
| CBD isolate* | — | 2.2 |
| Total | 100 | 100 |

The coating was applied as a pre-heated suspension as outlined above to 1.35 g tableted chewing gum with the formulation of CG100 in Example 15, except that CBD 52% or CBD isolate was substituted with isomalt in CG100. Hence, CBD was not present in the tableted chewing gum, but only in the coating. A total of 10 mg CBD was present in the coated tablet. The suspension was applied in 3 subsequent steps according to conventional coating techniques to a total of 0.45 g coating to the 1.35 g tableted chewing gum. This corresponds to a ratio of tableted chewing gum to coating on 75:25.

Example 24

In Vivo Testing of Release

A sample was chewed with a chewing frequency of 60 chews pr. minute for 3 or 5 minutes in a test panel of 8 test persons. The test person was a healthy person appointed on an objective basis according to specified requirements. After 3 or 5 minutes, the content of CBD was measured in the remaining chewing gum residue. The chewing gum was subject to triple measurements for each of the 8 test persons, giving a total of 24 measurements for each sample. An average of the 24 measurements was calculated and the weight % release was calculated based on the original content of CBD in the sample. The content of CBD was measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly to an HPLC system and analyzed by an assay method.

Example 25

In Vitro Testing of Release

In vitro release of CBD was established by means of a chewing machine (Dissolution Test for Chewing Gums, General Monograph 2.9.25. In European Pharmacopoeia, 5th ed). A chewing chamber was filled with 20 ml buffer (phosphate buffer pH 7.4). The chewing gum sample was placed in the chamber and the chewing machine was initiated at 20 degrees Celsius with 1 chew per second. After 3 or 5 minutes of chewing, the machine was stopped and the chewing gum sample (residue) was placed in a vial. If more release time points are needed (release profile), the chewing buffer must be exchanged with 20 ml of fresh buffer every five minutes. The content of CBD was measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method.

Example 26

Stability Testing Method

For stability testing, the ICH guideline is used; 25° C./60% RH (2 years), 30° C./65% RH (1 year), 40° C./75% RH (3 months). All samples were packed in duma bottles before stored in the conditions. All samples were sensorially and analytically evaluated. The content of CBD was measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC set-up and analyzed by an assay method. The following method was able to separate and quantify CBD, delta-9 THC, delta-8 THC and CBN.

Example 27

CBD Delivered to the Oral Mucosa

A sample was chewed in vivo with a chewing frequency of 60 chews pr. minute for 5 minutes in a test panel of 8 test persons. The test person was not allowed to swallow during the procedure. After one minute, saliva was obtained from the test person and collected in a vessel for later analysis. In tests for 5 minutes release, the same procedure was followed until 5 minutes where the last sample was collected and added to the same vessel for aggregated analysis. The test person was a healthy person appointed on an objective basis according to specified requirements. the aggregated saliva sample was collected after 5 minutes, the content of CBD was measured in the saliva. The content of CBD was also measured in the remaining chewing gum residue. The chewing gum residue was positioned in a flask and weighted. Subsequently, an organic solvent was added for dissolution purposes, and the mixture was mixed on a laboratory shaker overnight. The organic phase was diluted and centrifuged. The supernatant was injected directly into an HPLC system and analyzed by an assay method. The gum and saliva was subject to 3 triple measurements for each of the 8 test persons, giving a total of 24 measurement for each sample. An average of the 24 measurements was calculated and the weight % release was calculated. By comparing the amount of CBD in the remaining chewing gum residue and the amount of CBD in the saliva, the amount of CBD delivered to the oral mucosa could be estimated.

Example 28

Sensorics Evaluation Test Set-Up

Apart from release measurements, either in vivo or in vitro, as well as stability tests of the tableted chewing gum, sensorics tests were also performed to reveal very important characteristics and properties of the tableted chewing gum. These sensorics parameters are important as indicators of the structure of the chewing gum composition and the behavior of the gum when chewed. The structure is the underlying guidance as to how the chewing gum resembles the structure of a comparative chewing gum, which is set as the standard in the test series, i.e. the chewing gums are compared to each other in the test series of preferably 5 samples. The test set-up was composed of 8 test persons in a test panel. Each of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent and comparable to the standard, i.e. "+++++" means that the gum was comparable to the standard and "+" means that the gum was very far from comparable to the standard. "0" indicated that it was not tested.

Five different parameters were tested in a test panel:

| Initial chew | Texture | Flavor | Sweetness | Off-notes |
| --- | --- | --- | --- | --- |

"Initial chew"—the first impression of the gum when chewed within the first 30 seconds. For instance, a very hard and viscous structure gave a very low rating and a very brittle structure also gave a very low rating.

"Texture"—the overall impression of the gum after 30 seconds of chewing gum or when the gum has gained the structure of a steady state. For instance, a very hard structure gave a very low rating and a very smooth structure also gave a very low rating.

"Flavor"—the overall impression of the gum during chewing with respect to flavor. For instance, a very low flavor experience gave a very low rating and a too high flavor experience that was not comparable to the standard also gave a very low rating.

"Sweetness"—the overall impression of the taste of the gum during chewing with respect to sweetness. For instance, if the sweetness was decreasing rapidly a very low rating was given and if the sweetness was too high giving an uncomfortable feeling a very low rating was also given.

"Off-notes"—the overall impression of the off-note from the one or more cannabinoids in the composition during chewing. For instance, if off-notes (grass, bitter notes, irritation in the throat) were experienced in the throat, a low rating was given and if other uncomfortable sensations was experienced a low rating was also given.

Example 29

Sensorics Evaluation of Cannabinoid Chewing Gum

TABLE 2A

Evaluation of Examples 14-22 according to Example 28.

| CG | Initial chew | Texture | Flavor | Off-notes | Sweetness |
|---|---|---|---|---|---|
| CG 100 | +++++ | +++++ | ++++ | ++++ | ++++ |
| CG 101 | +++++ | +++++ | ++++ | ++++ | ++++ |
| CG 102 | +++++ | +++++ | ++++ | ++++ | ++++ |
| CG 103 | ++++ | +++ | +++ | +++ | ++++ |
| CG 104 | ++++ | ++++ | ++++ | ++++ | ++++ |
| CG 105 | +++++ | +++++ | ++++ | ++++ | ++++ |
| CG 106 | +++++ | +++++ | ++++ | ++++ | ++++ |
| CG 107 | +++++ | +++++ | ++++ | ++++ | ++++ |
| CG 108 | ++++ | +++ | +++ | +++ | +++ |
| CG 109 | +++ | ++++ | ++++ | +++ | +++ |
| CG 110 | 0 | 0 | ++++ | ++++ | +++++ |
| CG 111 | 0 | 0 | ++++ | +++++ | +++++ |
| CG 112 | 0 | 0 | +++++ | +++++ | +++++ |
| CG 113 | 0 | 0 | ++++ | ++++ | ++++ |
| CG 114 | 0 | 0 | +++++ | ++++ | +++++ |
| CG 115 | +++++ | +++++ | ++++ | ++++ | ++++ |
| CG 116 | +++++ | +++++ | ++++ | ++++ | ++++ |
| CG 117 | ++ | + | ++ | + | ++++ |
| CG 118 | + | + | ++ | + | ++++ |
| CG 119 | ++ | ++ | +++ | +++ | ++++ |
| CG 120 | ++++ | ++++ | +++ | +++ | +++ |
| CG 121 | +++++ | +++++ | ++++ | ++++ | ++++ |
| CG 122 | ++++ | ++++ | +++ | +++ | +++ |
| CG 123 | +++++ | ++++ | ++++ | ++++ | ++++ |
| CG 124 | ++ | ++ | +++ | ++ | ++ |
| CG 125 | +++ | +++ | ++++ | +++ | +++ |
| CG 126 | ++++ | ++++ | ++++ | ++++ | +++ |
| CG 127 | +++++ | +++++ | +++++ | +++++ | ++++ |
| CG 128 | +++++ | +++++ | +++++ | +++++ | ++++ |
| CG 129 | ++++ | ++++ | ++++ | +++ | +++ |
| CG 130 | +++++ | +++++ | +++++ | ++++ | ++++ |
| CG 131 | +++++ | +++++ | ++++ | ++++ | +++ |
| CG 132 | ++++ | ++++ | ++++ | +++++ | ++++ |
| CG 133 | ++++ | ++++ | ++++ | ++++ | ++++ |
| CG 134 | +++++ | +++++ | ++++ | ++++ | ++++ |
| CG 135 | ++++ | ++++ | ++++ | ++++ | ++++ |
| CG 136 | +++++ | +++++ | ++++ | ++++ | ++++ |
| CG 137 | ++++ | ++++ | +++ | ++++ | ++++ |
| CG 138 | +++++ | +++++ | +++ | +++ | ++++ |
| CG 139 | +++++ | +++++ | ++++ | +++++ | +++++ |
| CG 140 | +++++ | +++++ | ++++ | ++++ | ++++ |
| CG 141 | +++++ | +++++ | ++++ | ++++ | ++++ |
| CG 142 | ++++ | ++++ | ++++ | ++++ | ++++ |
| CG 143 | +++++ | +++++ | +++++ | ++++ | +++ |
| CG 144 | +++++ | +++++ | +++++ | ++++ | +++ |

Example 30

Release of Cannabinoid

TABLE 2B

Chewing gum samples from Example 14 was tested for release after 3 or 5 minutes of in vitro chewing according to the test method of Example 25. The value indicates weight % of cannabinoid released from the chewing gum sample (CG).

| CG Number | CG 100 | CG 101 | CG 102 | CG 103 | CG 104 |
|---|---|---|---|---|---|
| 3 minutes | 39 | 37 | 40 | 34 | 30 |
| 5 minutes | 43 | 42 | 44 | 38 | 36 |

The result shows that in the outer end of the ranges according to the invention, the release was lower, but still acceptable (CG103 and CG104). However, the ranges should be seen combined, such that the range of each of elastomer plasticizers and natural resin contributes in combination to the overall effect and release properties of the chewing gum. Hence, if an amount in the end of the range for natural resin is applied, the amount of elastomer plasticizer may to some extend counteract the negative effect.

Example 31

Release of Cannabinoid

TABLE 2C

Chewing gum samples from Example 15 was tested for release after 3 or 5 minutes of in vitro chewing according to the test method of Example 25. The value indicates weight % of cannabinoid released from the chewing gum sample (CG).

| CG Number | CG 105 | CG 106 | CG 107 | CG 108 | CG 109 |
|---|---|---|---|---|---|
| 3 minutes | 38 | 39 | 43 | 33 | 31 |
| 5 minutes | 43 | 44 | 45 | 37 | 35 |

The result shows that in the outer end of the ranges according to the invention, the release was lower, but still acceptable (CG108 and CG109). However, the ranges should be seen combined, such that the range of each of elastomer plasticizers and natural resin contributes in combination to the overall effect and release properties of the chewing gum. Hence, if an amount in the end of the range for natural resin is applied, the amount of elastomer plasticizer may to some extend counteract the negative effect.

The release of CG 110-114 was comparable to CG105-109.

Example 32

Release of Cannabinoid

TABLE 2D

Chewing gum samples from Example 17 was tested for release after 3 or 5 minutes of in vitro chewing according to the test method of Example 25. The value indicates weight % of cannabinoid released from the chewing gum sample (CG).

| CG Number | CG 115 | CG 116 | CG 117 | CG 118 | CG 119 |
|---|---|---|---|---|---|
| 3 minutes | 39 | 37 | 9 | 8 | 16 |
| 5 minutes | 43 | 42 | 17 | 16 | 19 |

The result is clear in the sense that addition of VA-VL to the composition provides a much lower release (CG 117-119) than by the use of the polymers and natural resin according to the present invention. In addition, the sensorics properties by the use of VA-VL (see above) also makes it clear that VA-VL is not preferred.

Example 33

Release of Cannabinoid

TABLE 2E

Chewing gum samples from Example 18 was tested for release after 3 or 5 minutes of in vitro chewing according to the test method of Example 25. The value indicates weight % of cannabinoid released from the chewing gum sample (CG).

| CG Number | CG 120 | CG 121 | CG 122 | CG 123 | CG 124 |
|---|---|---|---|---|---|
| 3 minutes | 31 | 39 | 30 | 38 | 10 |
| 5 minutes | 34 | 43 | 35 | 41 | 14 |

The addition of talc to the composition was expected to give a higher release of CBD since it was expected that talc would provide a more porous structure to the tableted chewing gum and thereby promote better release of CBD. However, this was not seen (CG120 and CG122) and it appears that the amount of sugar alcohols is more important for release characteristics than previously expected. With respect to the extruded gum reference example (CG124), it is seen that the release properties were significantly lower than the examples according to the invention.

Example 34

Release of Cannabinoid

TABLE 2F

Chewing gum samples from Example 19 was tested for release after 3 or 5 minutes of in vitro chewing according to the test method of Example 25. The value indicates weight % of cannabinoid released from the chewing gum sample (CG).

| CG Number | CG 125 | CG 126 | CG 127 | CG 128 | CG 129 |
|---|---|---|---|---|---|
| 3 minutes | 30 | 35 | 39 | 40 | 44 |
| 5 minutes | 34 | 41 | 43 | 46 | 56 |

The results shows that a low amount of sugar alcohol in the gum (CG125) has an effect on the release of cannabinoids and that a higher amount was desirable. However, a too high amount of sugar alcohol (CG129) affected other properties of the chewing gum as seen in the sensorics results which was not expected. It is noted that the release properties should be seen in combination with the sensorics properties.

Example 35

Release of Cannabinoid

TABLE 2G

Chewing gum samples from Example 20 was tested for release after 3 or 5 minutes of in vitro chewing according to the test method of Example 25. The value indicates weight % of cannabinoid released from the chewing gum sample (CG).

| CG Number | CG 130 | CG 131 | CG 132 | CG 133 | CG 134 |
|---|---|---|---|---|---|
| 3 minutes | 65 | 60 | 48 | 54 | 66 |
| 5 minutes | 68 | 63 | 54 | 58 | 70 |

The result shows that the best release rate was obtained with a formulation of CG130 and CG134. In these examples, the gum base content was lower than in CG131 and CG133. When CBD was located in the gum layer, the release was somewhat lower (CG132).

Example 36

Release of Cannabinoid

TABLE 2H

Chewing gum samples from Example 21 was tested for release after 3 or 5 minutes of in vitro chewing according to the test method of Example 25. The value indicates weight % of cannabinoid released from the chewing gum sample (CG).

| CG Number | CG 135 | CG 136 | CG 137 | CG 138 | CG 139 |
|---|---|---|---|---|---|
| 3 minutes | 37 | 34 | 32 | 71 | 65 |
| 5 minutes | 41 | 38 | 33 | 75 | 71 |

Generally, a slightly lower release was obtained when the content of gum base was increased, both in the two-layered tableted chewing gum and in the three-layered tableted chewing gum.

Example 37

Release of Cannabinoid

TABLE 2I

Chewing gum samples from Example 22 was tested for release after 3 or 5 minutes of in vitro chewing according to the test method of Example 25. The value indicates weight % of cannabinoid released from the chewing gum sample (CG).

| CG Number | CG 140 | CG 141 | CG 142 | CG 143 | CG 144 |
|---|---|---|---|---|---|
| 3 minutes | 39 | 17 | 19 | 46 | 49 |
| 5 minutes | 43 | 21 | 25 | 52 | 58 |

The overall result shows that release promoting systems, such as a cyclodextrin complex with CBD (CG143) or self-emulsifiers systems (CG144), may be a particular advantage according to the invention if a higher release is desirable. However, the use of microcrystalline cellulose as a carrier in a 10% MCC-system (CG142) did provide a lower overall release which was even lower for a 5% MCC-system (CG141).

Example 38

Coating with CBD

TABLE 3A

Chewing gum samples from Example 23 was tested for release after 3 or 5 minutes of in vitro chewing according to the test method of Example 25. The value indicates weight % of cannabinoid released from the chewing gum sample (CG).

| CG Number | CG 145 | CG 146 |
|---|---|---|
| 3 minutes | 60 | 55 |
| 5 minutes | 59 | 61 |

The result was highly surprising since it was expected that a major amount of CBD from the coating was absorbed in the chewing gum upon chewing. However, the result shows that application of one or more cannabinoids into a coating, such as a hard coating, may be a promising way to deliver cannabinoids. Also, by combining the application of one or more cannabinoids in the coating as well as in the tableted chewing gum, controlled release of cannabinoids may be obtained. This may also be used to provide a biphasic release of cannabinoids, such that an initial high release is provided by the coating and a more sustained release is provided by incorporating the cannabinoids in the tableted chewing gum.

Example 39

CBD Delivered to the Oral Mucosa

Tests were conducted in accordance with the test method of Example 27. The tests were performed for CG100 and CG101. The values for the CBD content in saliva and in the chewing gum residue were measured after 5 min of chewing. From these values, the content of CBD delivered to the oral mucosa could be calculated.

TABLE 3B

Chewing gum samples from Example 14 were tested for content of CBD delivered to the oral mucosa after 5 minutes of in vivo chewing according to the test method of Example 27. The values indicate weight % of cannabinoid based on the one or more cannabinoids present in the initial formulation.

| CG Number | CG 100 | CG 101 |
|---|---|---|
| CBD in saliva | 11 | 9 |
| CBD in residue | 57 | 58 |
| CBD delivered to mucosa | 32 | 33 |

The results of the tests were very surprising as a major part of the CBD released after 5 minutes of chewing was delivered to the oral mucosa. It was expected that a much higher amount of CBD was present in the saliva after 5 minutes of chewing, but only a relatively low amount of CBD was found in the saliva. Hence, the chewing gum formulation of the invention is very suitable for delivery of cannabinoids to the oral mucosa, much better than would have been expected.

Example 40

CBD Delivered to the Oral Mucosa

Tests were conducted in accordance with the test method of Example 27. The tests were performed for CG130 and CG131. The values for the CBD content in saliva and in the chewing gum residue were measured after 5 min of chewing. From these values, the content of CBD delivered to the oral mucosa could be calculated.

TABLE 3C

Chewing gum samples from Example 20 were tested for content of CBD delivered to the oral mucosa after 5 minutes of in vivo chewing according to the test method of Example 27. The values indicate weight % of cannabinoid based on the one or more cannabinoids present in the initial formulation.

| CG Number | CG 130 | CG 131 |
|---|---|---|
| CBD in saliva | 23 | 22 |
| CBD in residue | 32 | 34 |
| CBD delivered to mucosa | 45 | 44 |

The results of the tests were very surprising as a major part of the CBD released after 5 minutes of chewing was delivered to the oral mucosa. It was expected that a much higher amount of CBD was present in the saliva after 5 minutes of chewing, but only a relatively low amount of CBD was found in the saliva. Hence, the chewing gum formulation of the invention is very suitable for delivery of cannabinoids to the oral mucosa, much better than would have been expected.

Example 41

CBD Delivered to the Oral Mucosa

Tests were conducted in accordance with the test method of Example 27. The tests were performed for CG135 and CG136. The values for the CBD content in saliva and in the chewing gum residue were measured after 5 min of chewing. From these values, the content of CBD delivered to the oral mucosa could be calculated.

TABLE 3D

Chewing gum samples from Example 21 were tested for content of CBD delivered to the oral mucosa after 5 minutes of in vivo chewing according to the test method of Example 27. The values indicate weight % of cannabinoid based on the one or more cannabinoids present in the initial formulation.

| CG Number | CG 135 | CG 136 |
|---|---|---|
| CBD in saliva | 8 | 7 |
| CBD in residue | 59 | 62 |
| CBD delivered to mucosa | 33 | 31 |

The results of the tests were very surprising as a major part of the CBD released after 5 minutes of chewing was delivered to the oral mucosa. It was expected that a much higher amount of CBD was present in the saliva after 5 minutes of chewing, but only a relatively low amount of CBD was found in the saliva. Hence, the chewing gum formulation of the invention is very suitable for delivery of cannabinoids to the oral mucosa, much better than would have been expected.

Example 42

CBD Delivered to the Oral Mucosa

Tests were conducted in accordance with the test method of Example 27. The tests were performed for CG145 and CG146. The values for the CBD content in saliva and in the chewing gum residue were measured after 5 min of chewing. From these values, the content of CBD delivered to the oral mucosa could be calculated.

TABLE 3E

Chewing gum samples from Example 23 were tested for content of CBD delivered to the oral mucosa after 5 minutes of in vivo chewing according to the test method of Example 27. The values indicate weight % of cannabinoid based on the one or more cannabinoids present in the initial formulation.

| CG Number | CG 145 | CG 146 |
|---|---|---|
| CBD in saliva | 28 | 31 |
| CBD in residue | 41 | 39 |
| CBD delivered to mucosa | 31 | 30 |

The results of the tests were surprising as a very high amount of CBD released after 5 minutes of chewing was delivered to the oral mucosa. It was expected that a much higher amount of CBD was present in the saliva after 5 minutes of chewing. It was not expected that such a high content of CBD could be delivered to the oral mucosa with the present chewing gum formulation. In fact, the content of CBD would be higher if polysorbate was not applied in the coating suspension since polysorbate facilitates emulsifying properties of the saliva which prevent CBD to be delivered to the oral mucosa to an even higher degree.

By varying the content of CBD in the coating and the content of CBD in the chewing gum, a controlled delivery system may be established.

The invention claimed is:

1. A method of producing a tabletted chewing gum composition for oral administration of cannabinoids, the method comprising the steps of:
   i) feeding a gum composition comprising water-insoluble gum base into an extruder from one or more feeding inlets,
   ii) pressurizing the gum composition in the extruder while controlling temperature and pressure of the gum composition,
   iii) extruding the gum composition through a die means,
   iv) cutting the extruded gum composition in a liquid filled chamber, thereby obtaining a first population of particles comprising water-insoluble gum base,
   v) including the first population of particles with a second population of particles comprising water-soluble chewing gum ingredients, the second population of particles being free of water-insoluble gum base, thereby obtaining a chewing gum composition,
   vi) including the first population of particles with a third population of particles comprising one or more cannabinoids and one or more of sugar alcohols, sugars, and microcrystalline cellulose species, and
   vii) tableting the chewing gum composition in a tablet pressing apparatus, thereby obtaining a tabletted chewing gum composition.

2. The method according to claim 1, wherein the temperature of the gum composition is controlled to be above 90° C. during the pressurizing step.

3. The method according to claim 1, wherein the pressure of the gum composition is controlled to be of at least 5 bar during the pressurizing step.

4. The method according to claim 1, wherein the first population of particles, comprising the water-insoluble gum base, has an average diameter in a range from 0.1 to 2.5 mm.

5. The method according to claim 1, wherein the first population of particles is cooled in the liquid filled chamber to a temperature of 55° C. and below.

6. The method according to claim 1, wherein the first population of particles is cooled in the liquid filled chamber and transferred to a de-watering device.

7. The method according to claim 1, wherein the first population of particles is dusted or coated when conveyed to the tablet pressing apparatus.

8. The method according to claim 1, wherein a content of the water-insoluble gum base of the first population of particles is more than 90% by weight of the first population of particles.

9. The method according to claim 1, wherein a content of the water-soluble chewing gum ingredients of the second population of particles is more than 90% by weight of the second population of particles, the second population of particles being free of water-insoluble gum base.

10. The method according to claim 1, wherein the first population of particles is present in an amount of 20 to 60% by weight of the tabletted chewing gum composition.

11. The method according to claim 1, wherein the second population of particles is present in an amount of 40 to 80% by weight of the tabletted chewing gum composition.

12. The method according to claim 1, wherein the water-insoluble gum base is partly located in a first layer of the chewing gum composition and the water-soluble chewing gum ingredients are partly located in a second layer of the chewing gum composition.

13. The method according to claim 1, wherein the tabletted chewing gum composition consists of two layers where a first layer is cohered to and adjacent to a second layer.

14. The method according to claim 1, wherein the tabletted chewing gum composition consists of three layers where one middle layer is cohered to and adjacent to two outer layers.

15. The method according to claim 1, wherein the one or more cannabinoids are located in a second layer of the chewing gum composition.

16. The method according to claim 1, wherein the one or more cannabinoids are both comprised in a first layer of the chewing gum composition and in a second layer of the chewing gum composition.

17. The method according to claim 1, wherein the water-insoluble gum base comprises one or more natural resins in an amount of 10-40% by weight of the water-insoluble gum base, one or more elastomers in an amount of 3-30% by weight of the water-insoluble gum base, and one or more elastomer plasticizers in an amount of 8-50% by weight of the water-insoluble gum base.

18. The method according to claim 1, wherein an amount of the gum base in the chewing gum composition is 15-60% by weight of the tabletted chewing gum composition.

19. The method according to claim 1, wherein the one or more cannabinoids are present in an amount of 0.1 to 200 mg.

20. The method according to claim 1, wherein the one or more cannabinoids are selected from the group consisting of cannabidiol (CBD), cannabidiolic acid (CBDA), cannabidivarin (CBDV), and combinations thereof.

21. The method according to claim 1, wherein the one or more cannabinoids are selected from the group consisting of tetrahydrocannabinol (THC), tetrahydrocannabinolic acid (THCA), tetrahydrocannabivarin (THCV), and combinations thereof.

22. The method according to claim 1, wherein the one or more cannabinoids comprise at least one phytocannabinoid present in a cannabinoid extract having a content of terpenes and/or flavonoids.

23. The method according to claim 1, wherein the one or more cannabinoids comprise at least one isolated cannabinoid.

24. The method according to claim 1, wherein step vi) is conducted prior to step v).

25. A method of producing a tabletted chewing gum composition for oral administration of cannabinoids, the method comprising the steps of:
   i) feeding a gum composition comprising water-insoluble gum base into an extruder from one or more feeding inlets,
   ii) pressurizing the gum composition in the extruder while controlling temperature and pressure of the gum composition,
   iii) extruding the gum composition through a die means,
   iv) cutting the extruded gum composition in a liquid filled chamber, thereby obtaining a first population of particles comprising water-insoluble gum base,
   v) including the first population of particles with a second population of particles comprising water-soluble chewing gum ingredients and one or more cannabinoids, the second population of particles being free of water-insoluble gum base, thereby obtaining a chewing gum composition,
   vi) including the first population of particles with a third population of particles comprising one or more cannabinoids and one or more sugar alcohols, and
   vii) tableting the chewing gum composition in a tablet pressing apparatus, thereby obtaining a tabletted chewing gum composition.

26. The method according to claim 25, wherein step vi) is conducted prior to step v).

27. A method of producing a tableted chewing gum composition for oral administration of cannabinoids, the method comprising the steps of:
- i) feeding a gum composition comprising water-insoluble gum base into an extruder from one or more feeding inlets,
- ii) pressurizing the gum composition in the extruder while controlling temperature and pressure of the gum composition,
- iii) extruding the gum composition through a die means,
- iv) cutting the extruded gum composition in a liquid filled chamber, thereby obtaining a first population of particles comprising water-insoluble gum base,
- v) including the first population of particles with a second population of particles comprising water-soluble chewing gum ingredients, the second population of particles being free of water-insoluble gum base, thereby obtaining a chewing gum composition,
- vi) including the first population of particles with a third population of particles comprising one or more cannabinoids and one or more microcrystalline cellulose species, and
- vii) tableting the chewing gum composition in a tablet pressing apparatus, thereby obtaining a tableted chewing gum composition.

28. The method according to claim 27, wherein step vi) is conducted prior to step v).

29. A method of producing a tableted chewing gum composition for oral administration of cannabinoids, the method comprising the steps of:
- i) feeding a gum composition comprising water-insoluble gum base into an extruder from one or more feeding inlets,
- ii) pressurizing the gum composition in the extruder while controlling temperature and pressure of the gum composition,
- iii) extruding the gum composition through a die means,
- iv) cutting the extruded gum composition in a liquid filled chamber, thereby obtaining a first population of particles comprising water-insoluble gum base,
- v) including the first population of particles with a second population of particles comprising water-soluble chewing gum ingredients, the second population of particles being free of water-insoluble gum base, thereby obtaining a chewing gum composition,
- vi) including the first population of particles with a third population of particles comprising one or more cannabinoids and one or more sugars,
- vii) tableting the chewing gum composition in a tablet pressing apparatus, thereby obtaining a tableted chewing gum composition.

30. The method according to claim 29, wherein step vi) is conducted prior to step v).

31. An intermediate chewing gum product for oral administration of cannabinoids, the intermediate chewing gum product comprising the chewing gum composition according to claim 1.

* * * * *